US012805770B1

(12) United States Patent
Mandlekar

(10) Patent No.: US 12,805,770 B1
(45) Date of Patent: Nov. 24, 2026

(54) SYSTEMS AND METHODS FOR WELL-BEING AND GLUCOSE MONITORING

(71) Applicant: LUMOSFIT INC., San Jose, CA (US)

(72) Inventor: Hemamalini Mandlekar, San Jose, CA (US)

(73) Assignee: LUMOSFIT INC., San Jose, CA (US)

( * ) Notice: Subject to any disclaimer, the term of this patent is extended or adjusted under 35 U.S.C. 154(b) by 16 days.

(21) Appl. No.: 19/288,189

(22) Filed: Aug. 1, 2025

Related U.S. Application Data

(63) Continuation of application No. 18/460,059, filed on Sep. 1, 2023, now abandoned.

(Continued)

(51) Int. Cl.

| | |
|---|---|
| ***A61B 5/145*** | (2006.01) |
| ***A61B 5/00*** | (2006.01) |
| ***A61B 5/1455*** | (2006.01) |

(52) U.S. Cl.

CPC ........ *A61B 5/14532* (2013.01); *A61B 5/1455* (2013.01); *A61B 5/681* (2013.01)

(58) Field of Classification Search

CPC .... A61B 5/1455; A61B 5/14532; A61B 5/681

See application file for complete search history.

(56) References Cited

U.S. PATENT DOCUMENTS 5,774,223 A * 6/1998 Urakami .............. A61B 5/0059 356/394
6,990,364 B2 1/2006 Ruchti et al.

(Continued)

FOREIGN PATENT DOCUMENTS

CN 113143264 * 7/2021
JP 5455135 B1 * 3/2014

(Continued)

OTHER PUBLICATIONS

Javid et al. article titled "Noninvasive Optical Diagnostic Techniques for Mobile Blood Glucose and Bilirubin Monitoring," © 2018 Journal of Medical Signals & Sensors | Published by Wolters Kluwer-Medknow, Website: www.jmss.mui.ac.ir, DOI: 10.4103/jmss.JMSS_8_18 (15 pages).

(Continued)

*Primary Examiner* — Jennifer Robertson
*Assistant Examiner* — H.Q. Nguyen
(74) *Attorney, Agent, or Firm* — Aurora Consulting LLC; Kristen J. Hansen; Ashley Sloat

(57) ABSTRACT

A wearable device for noninvasive blood glucose monitoring includes at least one optical sensor communicatively coupled to at least one near infrared light source, the at least one optical sensor configured to sense reflected light from a body site resulting in capturing an image; and at least one processor communicatively coupled to the wearable device and configured to programmatically analyze the image to determine a blood glucose estimate for the subject. Analyzing may include: analyzing, by a machine learning model, a visual appearance of at least one venous blood vessel in a plurality of regions in the at least one digital image and classifying the plurality of regions according to predefined glucose levels; and generating, based on the classifying and on the visual appearance of the at least one venous blood vessel, a blood glucose estimate for the subject.

29 Claims, 15 Drawing Sheets

Related U.S. Application Data

(60) Provisional application No. 63/378,141, filed on Oct. 3, 2022, provisional application No. 63/403,742, filed on Sep. 3, 2022.

(56) References Cited

U.S. PATENT DOCUMENTS

| | | | | |
|---|---|---|---|---|
| 11,412,962 | B1 * | 8/2022 | Miller | A61B 5/4845 |
| 11,540,752 | B1 * | 1/2023 | Miller | A61B 5/681 |
| 2002/0028519 | A1 * | 3/2002 | Yguerabide | G01N 33/54313 436/518 |
| 2016/0058339 | A1 * | 3/2016 | Eguchi | A61B 5/489 600/310 |
| 2017/0340209 | A1 * | 11/2017 | Klaassen | A61B 5/021 |
| 2020/0211717 | A1 * | 7/2020 | Albert | A61B 5/00 |
| 2022/0079477 | A1 | 3/2022 | Deng | |
| 2024/0023838 | A1 * | 1/2024 | Valero de Clemente | A61B 5/0077 |

FOREIGN PATENT DOCUMENTS

| | | | | | |
|---|---|---|---|---|---|
| KR | 101491854 | B1 | * | 2/2015 | A61B 5/14532 |
| TW | M627646 | | * | 6/2022 | |
| WO | 9200513 | A1 | | 1/1992 | |
| WO | 2018214298 | A1 | | 11/2018 | |
| WO | WO-2022113608 | A1 | * | 6/2022 | A61B 5/14532 |

OTHER PUBLICATIONS

Wang et al. article titled “Modeling on the feasibility of camera-based blood glucose measurement,” provided by Computer Vision Foundation (identical to final published version of the proceedings on IEEE Xplore. (8 pages).

* cited by examiner

Glucose Meter reading: 93 mg/dL

Glucose Meter reading: 89 mg/dL

Glucose Meter reading: 98 mg/dL

Glucose Meter reading: 110 mg/dL

Glucose Meter reading: 98 mg/dL

Glucose Meter reading: 110 mg/dL

Glucose Meter reading: 82 mg/dL

Glucose Meter reading: 132 mg/dL

Glucose Meter reading: 96 mg/dL

Glucose Meter reading: 96 mg/dL

Glucose Meter reading: 71 mg/dL

Glucose Meter reading: 121 mg/dL

Glucose Meter reading: 97 mg/dL

Glucose Meter reading: 92 mg/dL

Glucose Meter reading: 91 mg/dL

Glucose Meter reading: 108 mg/dL

SYSTEMS AND METHODS FOR WELL-BEING AND GLUCOSE MONITORING

CROSS-REFERENCE TO RELATED APPLICATIONS

This application is a continuation of U.S. patent application Ser. No. 18/460,059, filed Sep. 1, 2023, which claims the priority benefit of U.S. Provisional Patent Application No. 63/403,742, filed Sep. 3, 2022, and U.S. Provisional Patent Application No. 63/378,141, filed Oct. 3, 2022, the contents of each of which are herein incorporated by reference in their entireties.

INCORPORATION BY REFERENCE

All publications and patent applications mentioned in this specification are herein incorporated by reference in their entirety, as if each individual publication or patent application was specifically and individually indicated to be incorporated by reference in its entirety.

TECHNICAL FIELD

This disclosure relates generally to the field of general wellness wearable devices, and more specifically to the field of diabetes related wearable devices. Described herein are systems and methods for well-being, glucose, and/or physiological monitoring.

BACKGROUND

The prevalence of diabetes, including type 2 diabetes (T2D), type 1 diabetes (TID), and prediabetes will increase to more than 54.9 million Americans by 2030 and is projected to cross half a billion people worldwide by 2040. Before developing T2D, most people have prediabetes; their blood sugar is higher than normal but not high enough yet for a diabetes diagnosis. While the prevalence of such conditions is predicted to increase substantially in the near future, proper blood glucose management can effectively reverse this condition, thus improving the health outcomes of these individuals. Several aspects of the etiology of T2D suggest that both high-risk and whole-population approaches are helpful to make a major impact on trends in the diabetes epidemic.

Self-monitoring of blood glucose (SMBG) is a helpful disease management component for improving patient/device user self-management and guiding clinicians in adjusting medications. SMBG data is used to improve glycemic control and identify hypoglycemic events, and also persistent hyperglycemia. The clinical utility of SMBG is dependent upon patients understanding the proper technique, being adherent to testing, and correctly interpreting the results. In addition, clinical utility comes from patients sharing their testing results with providers, and providers acting on that data to make treatment decisions.

Current SMBG methods using an invasive glucose monitor (IGM) involve poking a clean fingertip with a lancet to get a drop of blood and applying it to a test strip on the device which then displays the reading. These devices are invasive, painful, time-consuming, and a constant burden for the household budget. Invasiveness is a common and serious barrier to SMBG with the use of home IGM devices. Such IGM systems have been marketed for almost half a century and have undergone continual improvements to require less blood volume and shorter measurement times. Unfortunately, the cost, pain, blood waste, and finger calluses related to this method reduce patient enthusiasm for frequent glucose testing.

Current continuous glucose monitors (CGM) are prescription-only medical devices that are invasive and involve the physical insertion and permanent placement of a sensor into either the belly (adults and children) or the buttocks (children only). The sensor implantation site cannot be the same for the sequential application of sensors. Another restriction is that the sensor should not be used where the sensor may be rubbed by clothing (such as a belt, waist band, seat belt strap) or during sleep. Moreover, the sensor needs replaced about every 10 days. Finally, there may be variations between sensors, thereby making it important to learn how a newly inserted sensor is operating (i.e., it is accurate or by what margin of error is the sensor under measuring or over measuring) for that user when deciding whether to make treatment decisions based on the readings made by that sensor.

Non-blood glucose sensing technologies have been under development since the mid-1980s, yet relatively few have realized commercialization and received regulatory approval. These products include noninvasive optical glucose monitors (NIO-GM), noninvasive fluid sampling glucose monitors (NIFS-GM), and minimally invasive glucose monitors (MI-GM). These technologies are generally characterized as providing continuous or intermittent glucose measurements with minimal or no pain.

SUMMARY

Due to the limitations of the current SMBG approaches and the importance of SMBG for reversing prediabetes, alternative methods are needed that are affordable, user friendly, non-invasive, and that promote widespread adoption in the whole population.

In some aspects, the techniques described herein relate to a method for performing noninvasive blood glucose monitoring of a subject, the method including: causing a light source to illuminate a body site of the subject; receiving at least one digital image representing reflected light from the body site; programmatically analyzing the at least one digital image to assess blood glucose for the subject, the analyzing including: analyzing, by a first machine learning model, a visual appearance of at least one venous blood vessel in a plurality of regions in the at least one digital image and classifying the plurality of regions according to predefined glucose levels; and generating, based on the classifying and on the visual appearance of the at least one venous blood vessel, a blood glucose estimate for the subject; and generating an indication representing the blood glucose estimate.

In some aspects, the techniques described herein relate to a method, wherein analyzing the visual appearance of the at least one venous blood vessel in the plurality of regions includes: determining an intensity level of pixels representing a portion of the at least one venous blood vessel in the at least one digital image; and determining an osmolality level based on one or more features of the pixels representing the portion of the at least one venous blood vessel in the at least one digital image.

In some aspects, the techniques described herein relate to a method, wherein the one or more features include: a determined vessel diameter of the portion of the at least one venous blood vessel in the at least one digital image; and a determined volume of fluid in the portion of the at least one venous blood vessel in the at least one digital image.

In some aspects, the techniques described herein relate to a method, wherein the blood glucose estimate is expressed as one of: a range of values, a category in a plurality of categories, or In some aspects, the techniques described herein relate to a measurement estimated to be accurate within a predefined margin of error.

In some aspects, the techniques described herein relate to a method, wherein the light source is a near infrared light source.

In some aspects, the techniques described herein relate to having wavelengths ranging from about 700 nm to about 1200 nm.

In some aspects, the techniques described herein relate to a method, wherein the indication representing the blood glucose estimate includes application data configured to present the blood glucose estimate to the subject in one or more of: an email, a display screen, a text message, an audio entry, and a visual indicator within a computing device associated with the subject or a care provider of the subject.

In some aspects, the techniques described herein relate to a method, wherein the indication representing the blood glucose estimate is configured to be provided as a notification to one or more interested parties who have (a) indicated an interest in receiving notifications and (b) are approved by the subject.

In some aspects, the techniques described herein relate to a method, further including: monitoring, the subject over time, the monitoring including: causing the light source to illuminate the body site according to a predefined schedule; receiving additional digital images of the body site during the monitoring; and programmatically analyzing the additional digital images to determine a plurality of additional blood glucose estimates for the subject; and generating a visual mapping depicting the blood glucose estimate and the plurality of additional blood glucose estimates in a time-based graph.

In some aspects, the techniques described herein relate to a method, further including: generating a first set of measurements associated with features of the at least one venous blood vessel detected in the at least one digital image at a first point in time; generating a second set of measurements for at least one image of the additional digital images corresponding to the body site in the at least one digital image, the second set of measurements corresponding to the features of the at least one venous blood vessel at a second point in time; and comparing the first set of measurements to the second set of measurements to determine an updated glucose measurement for the subject.

In some aspects, the techniques described herein relate to a method, wherein the body site is a volar wrist of the subject and wherein the at least one digital image is captured by a sensor installed on a wearable device configured to be positioned on or adjacent to the volar wrist of the subject. 13.

In some aspects, the techniques described herein relate to a method, wherein: the body site is a dextral volar wrist of the subject and the light source is positioned on a sinistral dorsal wrist and facing away from the sinistral dorsal wrist; and the at least one digital image is of at least a portion of the dextral volar wrist that is captured in response to detecting that the dextral volar wrist is within a predefined range of the light source.

In some aspects, the techniques described herein relate to a method, further including: programmatically analyzing the at least one digital image against previously captured prior digital images of the body site to ascertain changes in blood glucose levels of the subject in response to an event, 16, wherein the event is one or more of: a meal, a fast, a physical stressor, an emotional stressor, a sleep event, a time of day, and a change in estrogen.

In some aspects, the techniques described herein relate to a method, wherein the at least one digital image is a sequence of frames of digital video.

In some aspects, the techniques described herein relate to a method, further including: segmenting, by a second machine learning model, the at least one digital image into the plurality of regions to detect the at least one venous blood vessel.

In some aspects, the techniques described herein relate to a noninvasive blood glucose monitoring system including: a wearable device configured to be removably coupled to a body site of a subject, the wearable device including: at least one optical sensor communicatively coupled to at least one near infrared light source, the at least one optical sensor configured to sense reflected light from the body site resulting in capturing an image; and at least one processor communicatively coupled to the wearable device and configured to programmatically analyze the image to determine a blood glucose estimate for the subject.

In some aspects, the techniques described herein relate to a noninvasive blood glucose monitoring system, wherein programmatically analyzing the image includes: analyzing, by a first machine learning model, a visual appearance of at least one venous blood vessel in a plurality of regions of the image and classifying the plurality of regions according to predefined glucose levels; and generating, based on the classifying and on the visual appearance of the at least one venous blood vessel, the blood glucose estimate for the subject; and generating an indication representing the blood glucose estimate. 21. 22.

In some aspects, the techniques described herein relate to a noninvasive blood glucose monitoring system, wherein analyzing the visual appearance of the at least one venous blood vessel in the plurality of regions includes: determining an intensity level of pixels representing a portion of the at least one venous blood vessel in the image; and determining an osmolality level based on one or more features of the pixels representing the portion of the at least one venous blood vessel in the image.

In some aspects, the techniques described herein relate to a noninvasive blood glucose monitoring system, wherein the one or more features include: a determined vessel diameter of the portion of the at least one venous blood vessel in the image; and a determined volume of fluid in the portion of the at least one venous blood vessel in the image.

In some aspects, the techniques described herein relate to a noninvasive blood glucose monitoring system, wherein the body site is an upper extremity of the subject, and the wearable device is configured to be positioned on or adjacent to the upper extremity. 26.

In some aspects, the techniques described herein relate to a noninvasive blood glucose monitoring system, wherein the body site is a dextral volar wrist and the wearable device is configured to: be positioned on a sinistral dorsal wrist with a detector of the optical sensor positioned opposite the sinistral dorsal wrist; and capture the reflected light from the dextral volar wrist in response to detecting that the dextral volar wrist is within a predefined range of the detector.

In some aspects, the techniques described herein relate to a noninvasive blood glucose monitoring system, further including: monitoring, the subject over time to capture additional images; programmatically analyzing the additional images to determine a plurality of additional blood glucose estimates for the subject; and generating a visual mapping depicting the blood glucose estimate and the plurality of additional blood glucose estimates in a time-based graph.

In some aspects, the techniques described herein relate to a noninvasive blood glucose monitoring system, further including: generating a first set of measurements associated with features of at least one venous blood vessel detected in the image of the body site at a first point in time; generating a second set of measurements for at least one image of the additional images corresponding to the body site in the image, the second set of measurements corresponding to the features of the at least one venous blood vessel at a second point in time; and comparing the first set of measurements to the second set of measurements to determine an updated glucose measurement for the subject.

In some aspects, the techniques described herein relate to a method for performing noninvasive blood glucose monitoring of a subject, the method including: causing a light source to illuminate a body site of the subject; receiving at least one digital image representing reflected light from the body site; programmatically analyzing the at least one digital image by at least one processor to assess blood glucose for the subject, the analyzing including: receiving an analysis output from a first machine learning model, the analysis output including one or more identified venous blood vessel portions in the at least one digital image, and a visual appearance assessment of the one or more identified venous blood vessel portions; and receiving based on the analysis output, a blood glucose estimate for the subject; and generating an indication representing the blood glucose estimate.

In some aspects, the techniques described herein relate to a method, wherein the first machine learning model and the second machine learning model are accessed on a cloud-based computing device by a noninvasive blood glucose monitor configured to monitor the subject.

In some aspects, the techniques described herein relate to a method, wherein the visual appearance assessment of the portion of the venous blood vessel includes: determining an intensity level of pixels representing a portion of the at least one venous blood vessel in the at least one digital image; and determining an osmolality level based on one or more features of the pixels representing the portion of the at least one venous blood vessel in the at least one digital image.

In some aspects, the techniques described herein relate to a method, wherein the one or more features include: a determined vessel diameter of the portion of the at least one venous blood vessel in the at least one digital image; and a determined volume of fluid in the portion of the at least one venous blood vessel in the at least one digital image.

In some aspects, the techniques described herein relate to a method, further including monitoring, the subject over time, to capture a plurality of additional images; programmatically analyzing the additional images to determine a plurality of additional blood glucose estimates for the subject; and generating a visual mapping depicting the blood glucose estimate and the plurality of additional blood glucose estimates in a time-based graph.

In some aspects, the techniques described herein relate to a method, further including receiving a segmentation output from a second machine learning model, the segmentation output including the identified venous blood vessel portions in the at least one digital image and image segments representing a plurality of regions of the at least one digital image.

BRIEF DESCRIPTION OF THE DRAWINGS

The foregoing is a summary, and thus, may be limited in detail. Approaches for performing a noninvasive blood glucose measurement and/or related prediction are presented herein. The above-mentioned aspects, as well as other aspects, features, and advantages of the present technology are described below in connection with various embodiments, with reference made to the accompanying drawings.

Figure 1:
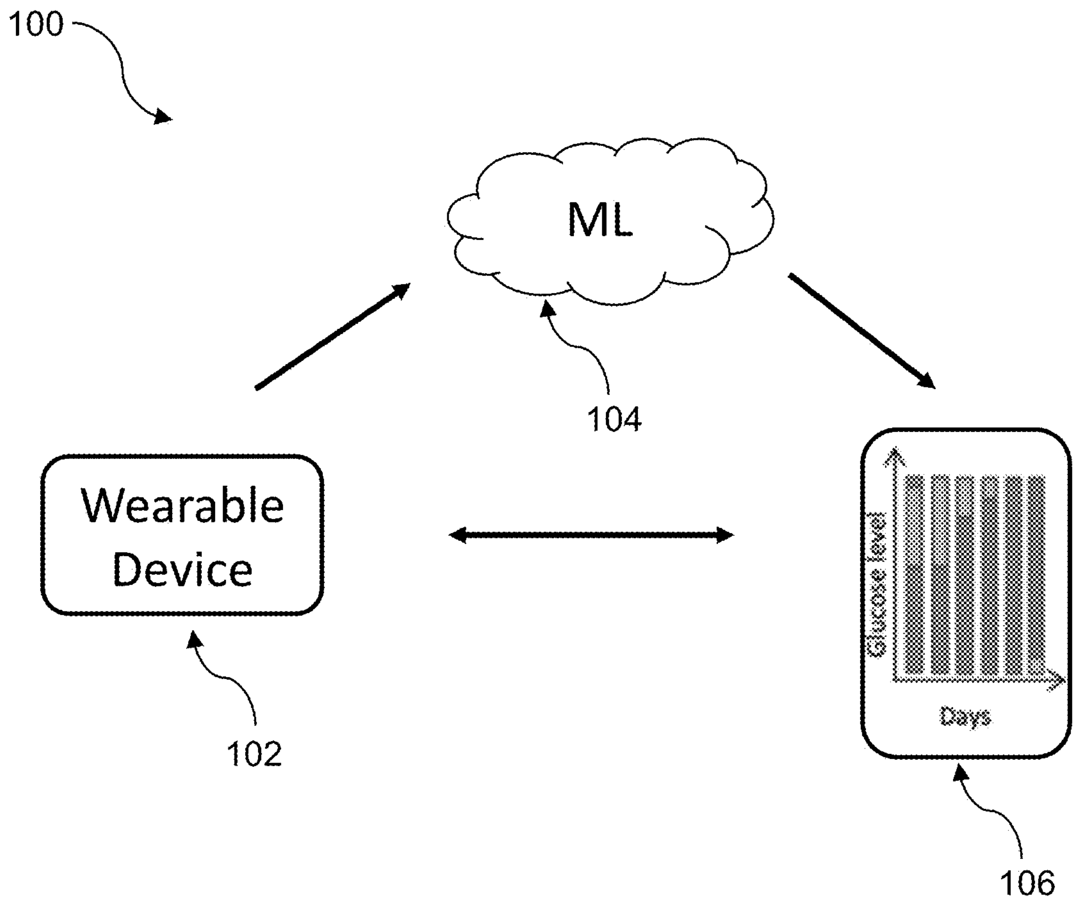
FIG. 1 is an example high level system for obtaining noninvasive glucose assessments for a body site of a user.

The illustrated embodiments are merely examples and are not intended to limit the disclosure. The schematics are drawn to illustrate features and concepts and are not necessarily drawn to scale.

DETAILED DESCRIPTION

The above-mentioned aspects, as well as other aspects, features, and advantages of the present technology will now be described in connection with various embodiments. The inclusion of the following embodiments is not intended to limit the disclosure to these embodiments, but rather to enable any person skilled in the art to make and use the contemplated invention(s). Other embodiments may be utilized, and modifications may be made without departing from the spirit or scope of the subject matter presented herein. Aspects of the disclosure, as described and illustrated herein, can be arranged, combined, modified, and designed in a variety of different formulations, all of which are explicitly contemplated and form part of this disclosure.

Described herein are systems and methods for non-invasive glucose monitoring. At a high level, the systems and methods described herein may monitor, determine, and inform the user about an anticipated or recent glucose reading and provide information about a recent trend in glucose readings for the user. In some embodiments, the systems and methods described herein can perform such monitoring to facilitate obtaining health knowledge for a user and to assist in user adherence to lifestyle improvements to reduce risks for developing blood sugar related illness, including, but not limited to: Type 2 Diabetes (T2D), Type 1 Diabetes (T1D), and prediabetes. In some embodiments, the systems and methods described herein may be used to enable early diagnosis of Type 2 Diabetes (T2D), Type 1 Diabetes (TID), and/or prediabetes. In some embodiments, the systems and methods described herein can generate predictive glucose responses and predictive health related events. In some embodiments, the systems and methods described herein can use data obtained from glucose monitoring to facilitate predictions that may be used to generate instructions for a user to carry out to treat, manage, and/or prevent blood sugar related illnesses.

The technical problem sought to be solved by the present disclosure is to provide non-invasive, near real time, and/or continuous glucose monitoring for a user. An example technical solution provided by the embodiments described herein includes employing at least one sensor device, software algorithms, and/or one or more ML models to assess changes over time in at least one body site of a user. The sensor device may include at least one image sensor (e.g., optical sensor, image capture device, camera, etc.) that may capture images of changes that occur in one or more veins (e.g., venous blood vessels) near to or at a surface of the body site of the user. For example, the sensors described herein may capture/observe a combined effect of both osmolality changes in an appearance of one or more veins of the body site and changes in a light absorption property of water and glucose associated with the one or more veins. These appearance changes may be used by the systems described herein to determine when a glucose level has changed for the user.

In some embodiments, the systems and methods described herein may provide a non-invasive optical sensor that detects a combined effect of both a certain physiological change in the human body and the physical light scattering property. Such changes/effects may be analyzed using a first machine learning (ML) model and/or a first Deep Learning (DL) model that may determine if the physical and/or physiological changes are coming from blood in the veins, for example. A second ML model 104*b* (which may represent a DL model) may map the changes in blood to a glucose level. A software application executing on a computer system (e.g., computer system 1400 of FIG. 14 and/or wearable device 102 of FIG. 2) may generate meaningful and actionable insights for a user wearing the optical sensor and/or a health care provider, a caretaker, or the like.

In general, the sensor devices described herein may capture images of the body site (e.g., veins, skin, etc.) and assess a darkness of the veins, a size of the veins, a volume of the veins, a skin texture, a skin color, a vein color, light backscatter, and/or absorption associated with the vein, each of which may be representative of particular particles, elements, or glucose flowing through the veins. For example, the systems described herein may assess a concentration of glucose, urea, sodium, chloride, potassium, and/or bicarbonate using a near infrared (NIR) optical sensor positioned substantially adjacent to a body site of a user to determine correlations between changes in blood glucose levels and changes in an appearance of the veins in images captured by the optical sensor.

The systems and methods described herein may provide the advantages of a wearable solution that reduces or eliminates the use of needle pricks, chemical patch replacements, under skin wire applications, or the in-clinic medical testing for blood sugar assessment. While there are numerous SMBG systems available, the embodiments described herein provide advantages compared to conventional solutions of blood sugar assessment and management.

For example, while conventional methods of non-invasive measures for SMBG have shown that they can provide reliable measurements related to blood glucose levels, such methods, despite these positive results, have been limited due to technical or usability issues with the approaches. For example, conventional methods of non-invasive measures for SMBG may include componentry that may be placed in body regions that may cause the componentry to be rubbed, moved, dislodged or the like. Such componentry may fail when improperly moved or dislodged. In some embodiments, conventional componentry for SMGB may also include electrochemical portions that have to be replaced or refilled.

The embodiments described herein may function to address at least the above limitations of conventional methods of SMBG. For example, the systems and methods described herein may provide a non-invasive and wearable glucose monitor that is an affordable, instantaneous, general wellness device. This device, coupled with a software application can function to provide meaningful and actionable blood sugar and/or general health insights for a particular user wearing the device. In addition, wearing one or more of the devices described herein may promote a healthy lifestyle ultimately helping users reverse prediabetes and/or prevent T2D. The systems and methods described herein provide at least the advantages of zero medical waste, user friendly interfaces, and in general, a low barrier to adoption thereby aiding widespread adoption.

In operation, the systems and methods described herein can illuminate a body site and capture images of the body site using an image sensor, such as an NIR optical image sensor (e.g., a camera) or a camera using a red-light source, to assess near infrared light absorption and scattering. For example, the image sensor may capture images of a body site of a user wearing a device housing the image sensor. The image sensor may capture images of a combined effect of both a physiological change in a human body and a physical light scattering property at the body site. In such examples, the body site may be illuminated with a wavelength of light in the range of highest sensitivity of the NIR sensor, that is, highest quantum efficiency of the NIR sensor and the light source wavelength may range from about 700 nm to about 1200 nm. The captured one or more images may be of any part of the human body. For example, a body site, as used herein may include one or more of a wrist (e.g., volar, dorsal), fingers (e.g., palmar or dorsal), an arm, a knee (e.g., popliteal fossa), a palm, a leg, an ankle, a foot, toes, etc. In operation, the systems and methods described herein may analyze captured images to determine the effects of physiological changes by analyzing how the body site scatters the illuminated light.

While the systems and methods described herein utilize the infrared or the near infrared spectrum to noninvasively assess glucose levels, spectroscopic techniques are not utilized in the techniques described herein. Instead ML models are generated and used to map image content of venous blood vessels to accurate glucose levels.

FIG. 1 is an example high level system 100 for obtaining noninvasive glucose assessments for a body site of a user.

The system 100 may use images and ML techniques to detect and analyze glucose signals associated with a body site of a user to determine whether the signals are coming from interstitial fluid or blood. For example, the system 100 may use one or more noninvasive optical sensors (e.g., image sensors 228) on a wearable device 102 to detect physical and physiological changes in venous blood under a skin portion of a user. In some embodiments, the wearable device 102 (and coupled image sensor 228) may be positioned against (or near to) the body site. In some embodiments, the wearable device 102 may be worn on a body part and the body site may be placed in contact (or in near contact) to the wearable device 102.

The image sensors 228 may include a light source, a red-light source, an IR light source, or a NIR light source for illuminating a body site. As a result, the incident light undergoes reflection, absorption, and scattering. The reflected light arrives at the image sensor (e.g., a camera lens). The camera lens focuses the reflected light onto a sensor which then produces an image that is captured using software. The digital image is stored on a persistent storage medium for later use by components of wearable device 102 and/or other computing device communicatively coupled to device 102.

The wearable device 102 may capture glucose signals (e.g., as images of the body site) and may utilize one or more ML models 104 (e.g., ML models 104*a*, 104*b*, 104*n*, etc.) to discern any physiological changes in glucose in the blood associated with the body site versus any physiological changes in glucose in the interstitial fluid associated with the body site. In some embodiments, the ML models 104 may map the detected changes in the blood to particular glucose levels. The device 102 may obtain additional glucose signals over time by monitoring the body site. Data may be generated from the monitoring, and the ML models 104 may analyze changes over time. Such changes and data may be generated by the ML models 104 using one or more processors as described herein, to generate user interface content and data for an application that may be presented on an optional display of the wearable device 102. Alternatively, the user interface content and/or data may be presented on a computing device 106 that is in wired or wireless communication with the wearable device 102. The computing device 106 may be a smart phone, a smart watch, a mobile gaming device, a laptop computer, a desktop computer, a cloud hosted computer, or the like.

In general, the generated user interface content and data may include at least actionable instructions and/or insights to a user wearing the wearable device 102. The actionable instructions and/or insights may provide the user with personalized feedback on how diet, exercise, and/or medications affect their blood glucose so that the user may use that information to adjust lifestyle choices.

Figure 2:
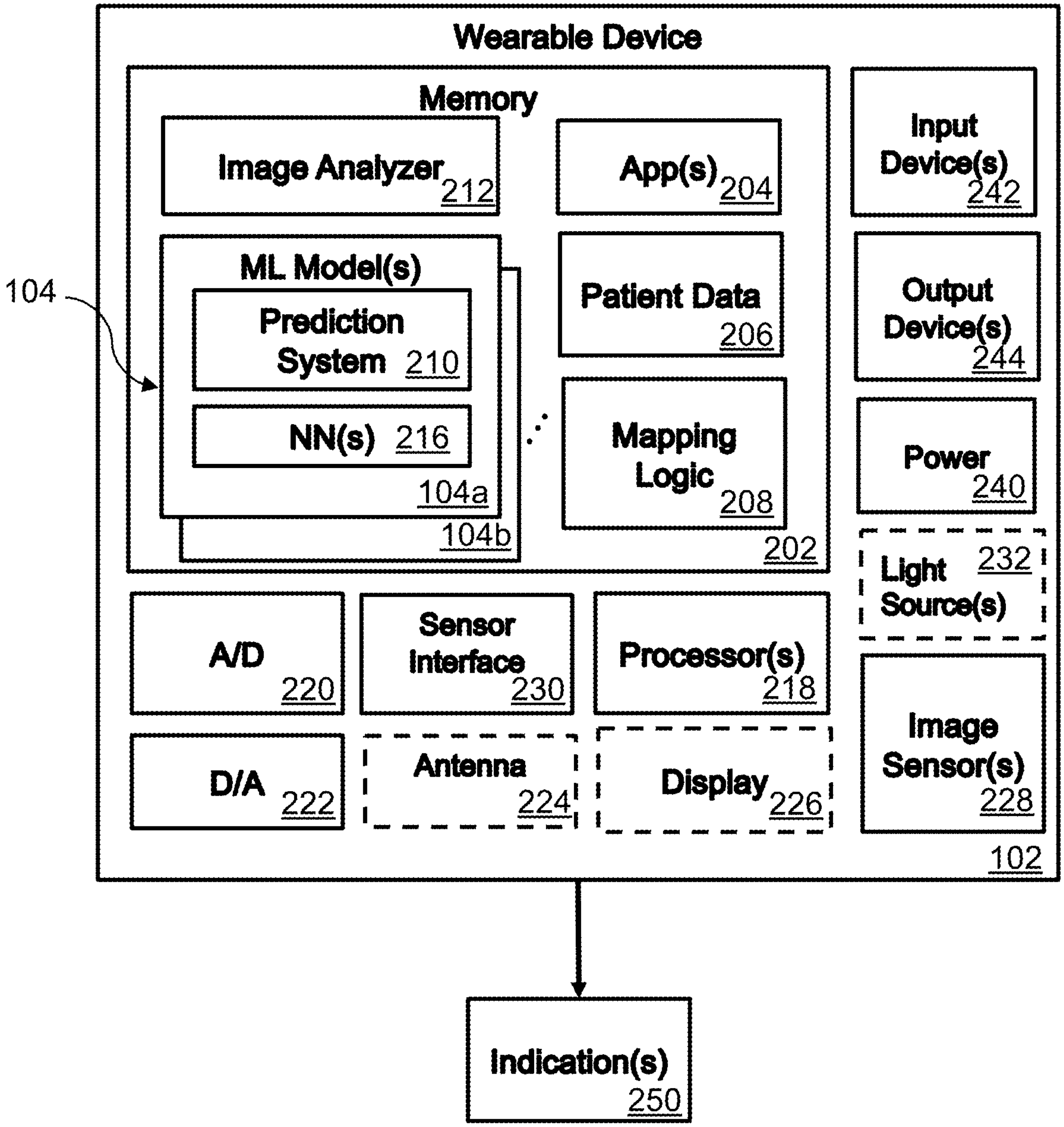
FIG. 2 is a block diagram of an example wearable device for monitoring well-being and/or glucose.

FIG. 2 is a block diagram of an example wearable device 102 for monitoring well-being and/or glucose. Some or all components of the wearable device 102 may be integrated into a band, a watch, a smart watch, an adhesive strip, jewelry, a patch, clothing, or any other wearable accessory. For example, some or all components of the wearable device 102 may be incorporated into a band or a watch or a pair of bands or pair of watches to be worn one on each arm or leg (or other appendage on the arm or leg). In some implementations, the band or watch may incorporate a stretchable or expandable element or stretch sensor to allow the band or watch to expand or stretch when a body portion near the band or watch swells. Non-limiting examples of a stretch sensor may include, but are not limited to, a strain gauge or an electrical component which can change inductance, resistance, or capacitance when stretched.

As shown in FIG. 2, the wearable device 102 includes memory 202 for storing program instructions and data that may be used and/or generated by processes carried out by the wearable device 102. The memory 202 may store and execute instructions associated with applications (e.g., apps) 204, patient data 206, mapping logic 208, prediction system 210, image analyzer 212, ML models 104, and/or neural networks 216. The processors 218, the analog to digital converter 220, the digital to analog converter 222, the optional antenna 224, and the optional display 226 may also interface with memory 202 and/or apps 204, patient data 206, mapping logic 208, prediction system 210, image analyzer 212, ML models 104, and/or neural networks 216, as described in detail below.

The wearable device 102 can include one or more sensors for detecting physiological parameters of the user. For example, the wearable device 102 can include one or more image sensors 228 for obtaining visually-identified glucose measurements, for example. Other sensors and/or elements may be incorporated into or near to the device 102. For example, other optical, electrical, and/or mechanical sensors may also be included in device 102 to measure any number of physiological parameters of a user wearing device 102.

In some embodiments, glucose measurements may be obtained using an optical sensor (e.g., one or more image sensors 228) that is integrated into or associated with the wearable device 102. For example, the device 102 may include one or more image sensors for detecting a combined effect of osmolality changes in one or more veins of the user by assessing an NIR light absorption property of water and a scattering property of glucose in the veins. In some embodiments, the image sensor 228 may be an NIR camera that captures images of veins in a body site of the user wearing device 102. In such an example, the image sensor 228 may operate with an optional light source 232 with a wavelength that ranges from about 700 nm to about 1000 nm. In some embodiments, the light source may be a red-light source with a wavelength of about 620 nm to about 750 nm. In some embodiments, the optional light source 232 may be integrated into the image sensor 228. In some embodiments, the optional light source 232 may be separate from image sensors 228, but may be installed within wearable device 102.

Alternatively, the device 102 may be communicatively coupled (e.g., via antenna 224) to an external sensor (not shown) that is not housed in or integrated into device 102. In such examples, the external sensor may provide data (e.g., images, measurements, etc.) to wearable device 102 to determine particular outputs, such as glucose levels, glucose predictions or related predictions, and/or other measurements obtained at a body site of the user wearing device 102 and/or the external sensor.

In some embodiments, the sensors 228 and/or other sensors in communication with wearable device 102 may be coupled to a sensor interface 230. The sensor interface 230 may store instructions to carry out operations pertaining to received sensor signals from one or more of the sensors 228. For example, the instructions may enable interaction with memory 202, one or more processors 218, and/or sensors 228 to communicate sensor data from one or more of the sensors 228 to the wearable device 102. The sensor data may be obtained from the sensors 228 in the form of recordings, measurements, images, and/or audial information.

Referring again to FIG. 2, the ML models 104 may include any number of neural networks 216 that are programmed to learn to determine levels of glucose in a vein, for example, by analyzing images of example veins (e.g., training data) at different levels of abstraction in order to determine levels of glucose in images of veins provided to the ML model 214 after the training of the model, for example. In general, the neural networks 216 can model complex non-linear relationships amongst inputs to learn how to analyze new inputs. The neural networks 216 may include or use one or more machine learning algorithms to learn from training data and apply that learning to new inputs. The learning may take the form of modeling high-level abstractions in data.

Although the prediction system 210 and NNs 216 are depicted in ML model 104*a*, each and every ML model 104*b* . . . 104*n*, etc. may include associated prediction systems 210 and/or NNs 216. In some embodiments, the ML models 104 share the prediction system 210 and the NNs 216.

In the examples described herein, the ML models 104 may be trained with training data including images of one or more veins of a user and with data representing glucose measurements, sodium measurements, and/or potassium measurements associated with blood of the respective user. For example, the ML models 104 described herein may be trained using (1) a collection of labeled data from clinical study participants to analyze a relationship between glucose, sodium, and/or potassium measurements associated with such study participants, (2) lab generated data values from a basic metabolic panel (BMP) testing and/or analysis. In some embodiments, an example clinical study may include about 20 to about 60 participants that are provided a controlled meal prior to a blood draw. Then, blood from a vein for each participant may be sampled (e.g., drawn at regular intervals of about 10 to about 15 minutes for about 3 hours). These blood samples can be run through a lab for BMP testing and/or analysis to obtain a reference value of each participant's blood glucose, sodium, potassium, and blood urea nitrogen (BUN), or other patient data 206, for example. The ML models 104 may be trained and tested to output a glucose value (or range) for a user wearing the wearable device 102, for example, based at least in part on elements (1) and (2) above. Although a single clinical study is described, any number of clinical studies and/or any amount of simulated data may be used to train and/or test the ML models 104.

In some embodiments, the training may include augmentation of datasets used for training. For example, training data may include preprocessing of data used for training. Preprocessing may include, but is not limited to resizing, rescaling, sampling, cropping, rotating, flipping, de-noising, etc. one or more of the images in the training data. In some embodiments, training data may include synthesized new data based on plausible and tested real-life scenarios for a particular user or a population.

The ML models 104 may include a first ML model 104*a* arranged to perform semantic segmentation on images to detect veins (e.g., portions of venous blood vessels). The first ML model 104*a* may perform image segmentation to partition a digital image into multiple segments. This segmenting process may simplify and/or modify a representation of the digital image as a basis in which to locate particular objects, boundaries, or the like within the images. For example, the segmenting process may be performed to identify one or more venous blood vessels and/or venous blood vessel portions within a body site adjacent to the wearable device 102.

In general, the segmenting process may include dividing up one or more digital images (e.g., representing a capture of IR reflections by sensor 228) and analyzing the one or more digital images. The analyzing may result in identifying particular pixels/voxels in the images and/or applying labels, indicators, markers, or other indications on particular pixels/voxels. In some embodiments, identifying and/or labeling pixels/voxels may pertain to venous blood vessels and/or particular changes in an appearance of such blood vessels. In some embodiments, identifying and/or labeling particular pixels/voxels may pertain to particular changes in light scattering behavior detected from the blood vessels. In some embodiments, identifying and/or labeling particular pixels/voxels may pertain to particular changes in osmolality changes associated with the digital images of the blood vessels. In some embodiments, identifying and/or labeling particular pixels/voxels may pertain to detecting a reduced scattering coefficient detected in the digital images of the blood vessels.

In some embodiments, segmenting and labeling the digital images may allow that particular features or characteristics in the segmented images be mappable back to features in a corresponding captured image in which the segmented images were derived. In some embodiments, the segmenting process may be used to train the first ML model 104*a* to segment structural features of blood vessels captured in images by wearable device 102.

The first ML model 104*a* may be one of several ML models within the ML models 104. The first ML model 104*a* may include a convolutional neural network (CNN) architecture such as a UNET, EFFICIENTNET, or RESNET. The first ML model 104*a* may be trained to segment venous blood vessel images and may be understood to include a collection of weights and biases for neurons established during training and details of hyperparameters such as the learning rate associated with the ML model. In some embodiments, patient data 206 may be used as training data in the event that the user (i.e., the patient under test) has approved the use of such data.

A second model 104*b* may receive the output (e.g., segmented images of one or more veins) of the first model as input and may perform a classification of the images. For example, a second model in the ML models 104 may include a CNN architecture (e.g., such as one or more deep learning networks) that may be used for classification of the segmented images into classes of glucose measurements having a range of about 5 mg/dL. The second ML model 104*b* may be trained to assess venous blood vessel images for blood glucose, sodium, bicarbonate, and/or potassium and may be understood to include a collection of weights and biases for neurons established during training and details of hyperparameters such as the learning rate associated with the ML model. In some embodiments, patient data 206 may be used as training data in the event that the user (i.e., the patient under test) has approved permission of the use of such data.

In some embodiments, the classification may be based on particular classes (e.g., categories) of glycemia associated with the glycemic index of food. In one non-limiting example, a size of each class may be chosen to be about 5 mg/dL per class. However, the total number of output classes utilized by device 102 and ML models 104 may be selected based on the size of each class. For example, the total number of output classes may be determined based on a clinically significant glucose range of about 54 mg/dL to about 250 mg/dL and a range of glucose values obtained from training data. In some embodiments, the number of output classes may be based on predetermined glucose ranges that are clinically significant. In some embodiments, the classification of the segmented images may be classified by the first ML model into classes selected based on one or more clinical trials. Such trials may collect (from each participant in a particular trial) images of venous blood vessels and corresponding blood samples at a same time window and/or before/after the time window. The blood samples may be tested for glucose, potassium, sodium, and/or BUN by a laboratory. Features in the images may be compared to levels of glucose, potassium, sodium, and/or BUN in the blood. Assessments may be made to generate the categories of glycemia. In some embodiments, the categories may be generated and subcategorized according one or more of subject age, disease status, weight, medication status, etc.

Upon completion of classification, the training of ML models 104 may be considered completed such that the ML models 104 can be used to infer a range of glucose values (e.g., mg/dL), given a sensor output from one or more sensors 228, for example.

In some embodiments, the ML models 104 may be expanded and trained to predict a range of glucose values according to a panel of metabolic readings, including, but not limited to potassium, sodium, and/or BUN, to provide an overall representation of current metabolic status related to prediabetes, for example. In some embodiments, the ML models 104 may be programmed to determine a maximum achievable accuracy, sensitivity, and/or specificity for glucose, potassium, sodium, and/or BUN values. Other patient data 206 may also be used for particular calculations and/or related predictions generated by device 102 when the user (i.e., the patient under test) has provided permission for the use of such data.

Example ML models 104 may include a CNN architecture that executes using two or more graphical processing units. For example, a CNN architecture like EFFICIENTNET or RESNET model may be used. In some embodiments, pre-training one or more of the ML models 104 with IMAGENET may be performed to assess and/or improve the accuracy of the output of one or more of the ML models 104. Bias, variance, and error analysis may be performed, on the development set, and appropriate model hyperparameters can be fine-tuned to iteratively increase the performance of the ML models 104. Further, different layers of the neural networks 216 can be introspected to understand what the different hidden units in both the shallow and deep layers of the networks are learning or computing. Information from neural network introspection may also be used to improve the performance of one or more of the ML models 104. Data visualization may be performed using t-SNE, for example, to understand how the output data is clustered and whether there are gaps in the output data.

In some embodiments, the performance of the ML model may be assessed (or results may be displayed) by an app 204 or server/cloud device (not shown). The assessment may evaluate according to any or all of the following elements: sensitivity, specificity, true/false positive, and true/false negative. The sensitivity element may refer to a probability of a positive test, conditioned on truly having a condition such as prediabetes, diabetes, etc. (or tested positive by a predefined test level if the true condition cannot be known). The specificity element may refer to a probability of a negative test, provided one does not have the condition. The true positive element may represent a test result that correctly indicates the presence of a condition or characteristic. The true negative element may represent a test result that correctly indicates the absence of a condition or characteristic. The false positive element represents a test result which wrongly indicates that a particular condition or attribute is present. The false negative element may represent a test result which wrongly indicates that a particular condition or attribute is absent.

In some embodiments, one or more user interfaces may be provided on the optional display 226 of wearable device 102 and/or another computing device coupled to wearable device 102. The user interfaces may be textual, tactile, audial, and/or graphical and may be displayed in one or more apps 204. The apps 204 may provide information (via the user interfaces) to support user self-monitoring with the intention of influencing health decisions to prevent the development of prediabetes and/or T2D. In some embodiments, one or more apps 204 may trigger for the sensor 228 to capture one or more images. The one or more images may then be sent to an external computing device (e.g., cloud server, mobile phone, computing system 1400, or the like) for further assessment and machine learning-based predictions. Any predicted results (e.g., glucose results, potassium results, sodium results, etc.) may be provided back to the app 204, which may cause display of such results on wearable device 102 (or another computing device external to device 102). In some embodiments, one or more apps 204 may trigger for the sensor 228 to capture one or more images. The one or more images may then be analyzed by wearable device 102 to perform assessment and machine learning-based predictions. Any predicted results (e.g., glucose results, potassium results, sodium results, etc.) may be provided via the app 204, which may cause display of such results on wearable device 102 (or another computing device external to device 102).

In some embodiments, an app(s) 204 may provide graphical content showing a current glucose, sodium, potassium, and/or BUN range for a user wearing device 102. For example, the app 204 can provide a graphical plot of one or more values throughout a time period, for example a day. This graphical plot and/or view may also mark hyper- and hypo-glycemic boundaries. In some embodiments, the apps 204 may provide a number to serve as a surrogate for good glycemic control and set targets for the user to help achieve specific glycemic control ranges. These targets can be set in an incremental way such that the user is able to gradually change behavior to achieve realistic and lasting lifestyle changes. In some embodiments, the apps 204 may be synchronized with a third party health app to provide users a holistic view of their glucose, metabolites, diet, and/or activity, just to name a few examples.

In general, the apps 204 may be used by a user of the wearable device 102 to interface with output from ML models 104, sensors 228, prediction system 210, image analyzer 212, and mapping logic 208. In some embodiments, at least one of the apps 204 may provide a trigger for a sensor (e.g., sensor 228) to capture data, send the captured data to an online storage medium (e.g., a cloud server) for ML processing and/or prediction system processing, and push the predicted results back to the app 204. The app 204 may then display the predicted results on the optional display 226, and/or may display results on another computing device display.

Referring again to FIG. 2, the image analyzer 212 may receive images (e.g., image data) from one or more image sensors 228 (e.g., an NIR sensor). The received images may include data representing one or more digital images capturing a body site of a user wearing device 102. The image analyzer 212 may assess the images to measure and/or detect both physical and physiological changes under human skin, such as within veins and in particular, venous blood. The physical and/or physiological changes in a vein responsive to IR light, for example, may be used by device 102 to ascertain changes in glucose for the user wearing device 102. For example, the changes in the darkness of one or more veins at the body site may be attributed to IR light interactions between the sensor 228 and the body site. Changes in the size and/or volume of the one or more veins at the body site may be attributed to osmolality changes.

In general, osmolality is a colligative property of a solution (including body fluid) that indicates the concentration of all the particles dissolved in the solution. Assessing osmolality using IR light, as described herein, can allow for determination of glucose changes in venous blood within a vein at a body site. In human blood serum or blood plasma, osmolality depends on the concentration of five major osmotic solutes. Three of the five osmotic solutes are of ionic nature (i.e., $Na+$ (sodium ion), $Cl-$ (chloride), $HCO3-$ (bicarbonate)). The final two osmotic solutes are non-ionic (i.e., glucose and urea). Water normally flows from a compartment of low osmolality to a compartment of high osmolality and this occurs if a membrane between the two compartments is permeable to water. When water moves between plasma and intracellular compartments, the movement direction depends on the osmolality of both compartments. For example, if a cell is in a relatively hyperosmolar solution, fluid will move out of the cell towards the highly concentrated compartment to reach homeostasis. As a result, the cell will shrink. There are many ways to estimate serum osmolality utilizing the basic metabolic panel test to measure sodium, glucose, potassium, and/or blood urea nitrogen.

In addition, water absorption in the shorter NIR wavelengths is typically lower (e.g., about 0.004 $mm^{-1}$ to about 0.04 $mm^{-1}$). Tissue penetration in the shorter NIR wavelengths is typically higher (e.g., about 2 mm to about 3 mm). Both together make this wavelength range suitable for sensing in humans. Clinical measurements corresponding to embodiments shown in FIGS. 4A-12D indicate a good correlation between reduced scattering coefficients of intracellular mediums and extracellular mediums in the NIR range and the concentration of glucose as determined from a conventional blood test of glucose.

The majority of glucose in the human body is found within interstitial fluid (i.e., between cells), rather than being contained in blood. Accordingly, the embodiments described herein may discern a location of one or more veins, determine where the one or more veins are located in relation to surrounding tissue, and perform analysis on changes over time in such veins and surrounding tissue. In addition, water also has a strong absorption spectrum in the NIR wavelengths. However, interference from water may be avoided by the embodiments described herein due to the ability of the wearable device 102 to discern veins from other tissues of the body. Further, under normal bodily function circumstances, the concentration of water in venal blood remains steady and thus is unlikely to interfere with assessments performed by the device 102 on captured images of the one or more veins.

Since glucose levels fluctuate immediately with food intake but sodium levels do not typically fluctuate immediately with food intake, changes in osmolality may predominantly reflect changes in blood glucose. Thus, the image analyzer 212 can obtain and analyze images and/or image data and provide such image data and analysis to one or more ML models 104. In some embodiments, one or more ML models 104 can preprocess (e.g., resizing, rescaling, sampling, cropping, rotating, flipping, etc.) the images before the image analyzer 212 analyzes the images. In some embodiments, the image analyzer 212 is a module within an ML model 104 and may function as an image analyzer algorithm for the ML model 104.

In general, the prediction system 210 may function with ML models 104 to preprocess, optionally segment, analyze, and predict blood glucose levels within one or more venous blood vessels. For example, the prediction system 210 may generate one or more outputs such as glucose levels, glucose measurements, glucose predictions, and/or related predictions. In some embodiments, the prediction system may generate the one or more outputs and wearable device 102 may use such outputs to generate indications 250. For example, prediction system 210 may be used to predict sodium, potassium, glucose, and/or BUN since serum osmolality is based on these metabolites. Prediction system 210 may use one or more of the following algorithms to predict sodium, potassium, glucose, and/or BUN.

$$(1.86\times Na)+(glucose/18)+(BUN/2.8)+9 \qquad \text{Algorithm one:}$$

$$(2\times Na)+(glucose/18)+(BUN/1.8) \qquad \text{Algorithm two:}$$

$$(1/86\times(Na+K))+(1.15\times(glucose/18))+(urea/6)+14 \qquad \text{Algorithm three:}$$

In some embodiments, ML models 104 may include a plurality of layers. For example, one or more shallow or lower layers may learn simple features, and one or more deeper layers may learn more complex features. In one exemplary, non-limiting embodiment, a first layer may learn simple features like edges (vertical, horizontal, diagonal) or shades of color. A second layer may learn more complex features such as shapes and textures. A third layer may learn further complex patterns like honeycomb shapes, multi-layered or dimensional shapes, etc. A fourth layer may be able to detect whole objects. A fifth layer may learn features within whole objects or associated with whole objects. Employing exemplary ML models 104 to the embodiments described herein may include using one or more lower layers to detect edges of veins, sizes of veins, shapes of veins, their color contrast, etc. Further, one or more deeper layers may be used to learn a wrist, background, fingers, whole arm, etc. Since the ML model 104 would be able to learn the shapes of veins, color contrast, and the size of the veins, the ML model 104 may learn to detect changes in the size, shape, and/or color of the veins. In other words, the ML model 104 may detect osmolality changes associated with one or more veins. In some embodiments, one or more connected layers may classify the various changes in size, shape, and/or color into probabilities of each glucose range, as described elsewhere herein.

Indications 250 may be provided and/or presented as text, audio data, and/or visual data including, but not limited to: observations, observation periods, glucose statistics, severity levels, raw measurements, predictive events, and predictive levels of glucose, etc. In some embodiments, the data may further include treatment options, diagnoses, activity levels, patterns in glucose over time, and/or other fitness or health measurements. For example, data may include reports with detailed analyses of glucose level predictions as well as various treatment options for a specific user. In some embodiments, alerts, messages, and/or reminders about particular glucose testing (e.g., image capture) and glucose assessments (e.g., data and/or reports that are generated on a schedule) may notify the user with a visual or audial cue.

The prediction system 210 may be part of ML models 104 and may utilize ML models 104 and/or image analyzer 212 to generate predictions of glucose levels over time based on captured images and/or reflections from a body site of a user wearing device 102, for example. In some embodiments, the prediction system 210 may determine or predict blood glucose measurements/estimates of a user wearing device 102 by using dynamic image attributes of a body site of the user from one or more sensors 228 on device 102.

In some embodiments, the prediction system 210 represents a diabetes classification system that may predict a likelihood of a user having and/or developing prediabetes, T2D, or another blood sugar disorder based on classifying glucose levels identified by ML models 104 by assessing images of venous blood vessels of a subject (e.g., user) wearing device 102, for example. In some embodiments, the prediction system 210 may further provide predictions for the user with respect to health decline or health improvement based on glucose levels that are determined over time for a particular user.

Predictions may be provided and/or presented as a report including data such as observations, observation periods, glucose statistics, severity levels, raw measurements, etc. In some embodiments, report data may further include treatment options, diagnoses, activity levels, patterns in glucose over time, and/or other fitness or health measurements. For example, reports may include detailed analysis of predictions as well as various treatment options for a specific user. In some embodiments, alerts, messages, and/or reminders about particular glucose testing (e.g., image capture) and glucose assessments (e.g., reports that are generated on a schedule) may notify the user with a visual or audial cue. For example, a visual cue may refer to a message indicator (e.g., indication(s) 250) in an app 204 or an email in an email app. An audio cue may be provided as an audio output from a speaker of device 102, an audio output from a digital assistant in communication with device 102, and/or an audio output from other computing device in communication with device 102.

In some embodiments, the ML models 104 may map the detected changes in the blood to particular glucose levels. The device 102 may obtain additional glucose signals over time by monitoring the body site. Data may be generated from the monitoring and the ML models 104 may map changes over time. In some embodiments, the mapping logic 208 may be used in combination with ML models 104 to map the detected changes in blood to particular glucose levels. For example, one or more images may be obtained from sensor 228. The one or more images may visually show a correlation between a change in a glucose level associated with one or more veins (captured in the one or more images) and a change in an appearance (e.g., a darkness, a size, and a volume) of the one or more veins. The visual changes in the vein can be mapped by ML models 104 using mapping logic 208 to map the visual features/changes to known glucose values.

The mapping logic 208 may represent a set of rules for mapping visual features/changes of a particular image of venous blood vessels to predefined glucose values. For example, the mapping logic 208 may include one or more data structures that correlate blood glucose levels with physical and/or physiological features of a venous blood vessel. The one or more data structures may include one or more lookup tables, algorithms, or techniques. The mapping logic 208 may be applied to function on pixels, voxels, circles, ovals, rectangles, squares, and/or other polygon or predefined shape.

In an exemplary, non-limiting embodiment, mapping logic 208 may include using an edge detector algorithm to detect the edges of one or more blood vessel portions in one or more images; segmenting image portions of the one or more blood vessel portions based on the detected edges; aligning the segmented image portions over time or from two or more time periods; determining a blood volume change between a first image, at a first time, showing the one or more blood vessel portions and a second image, at a second time, showing the one or more blood vessel portions; detecting, using a contrast detector, a change in the darkness or intensities of the pixels between a first image, at a first time, showing the one or more blood vessel portions and a second image, at a second time, showing the one or more blood vessel portions; and mapping the change in darkness or intensities to a corresponding change in a glucose level done based on the determined changed in blood volume and the determined change in darkness or intensities of the pixels. In some embodiments, the first time and the second time are after a predefined event, event-based, on-demand, otherwise. The events may include, but are not limited to, one or more of: a meal, a fast, a physical stressor, exercise, an emotional stressor, a sleep event (e.g., excess sleep, sleep deprivation, exhaustion, etc.), a time of day, and a change in estrogen.

These changes in an appearance (e.g., darkness, size, and volume) of the one or more veins, as captured by the sensor 228, can be ascertained by the device 102 and ML models 104 based on a combined effect of the reduced scattering coefficient of NIR light in the presence of glucose molecules and the change in plasma osmolality as described in detail herein. Determining changes in the appearance of one or more veins of a user wearing device 102, for example, can be used as a way to measure venous blood glucose values for the user in a noninvasive way by using image capture and machine learning image assessments.

In some embodiments, the ML models 104 may utilize mapping logic 208 to map detected changes in the appearance of veins before and after events. The events may include, but are not limited to one or more of: a meal, a fast, a physical stressor, exercise, an emotional stressor, a sleep event (e.g., excess sleep, sleep deprivation, exhaustion, etc.), a time of day, and a change in estrogen. In some embodiments, using ML models 104 to map detected changes in the appearance of veins before and after events allows the learned patterns and predictions (generated by ML models 104) about glucose determinations and/or related predictions to be incorporated into a semi-supervised ML learning stage of ML models 104. For example, a semi-supervised stage of an ML model may include learning from both unlabeled and labeled samples, typically sampled from the same or similar distributions. In some embodiments, using ML models 104 to map detected changes in the appearance of veins before and after events allows the learned patterns and predictions (generated by ML models 104) about glucose determinations and/or related predictions to be incorporated into a self-supervised ML learning stage of ML models 104.

In some embodiments, one or more of ML models 104 may employ self-supervised learning. Self-supervised learning uses surrogate (pretext) tasks that can be formulated using unsupervised data. A pretext task is designed in a way that solving the pretext task includes learning of a useful image representation. In some of the embodiments described herein, the pretext task may be learning representations by maximizing agreement between different views of the veins of each user obtained at the same instant of time. For example, the process may include supervised pretraining using large scale non-medical labeled data (e.g., ImageNet). The process may further include multi-instance contrastive self-supervised pretraining using domain specific unlabeled data, resulting in learning a representation or pretext task. For example, an unlabeled dataset may be collected from any of the devices described herein without a clinical study because the data is unlabeled (i.e., does not include corresponding venous blood glucose values). The process may further include supervised fine-tuning using labeled dataset collected from, for example, a clinical study. This may be the classification step that learns to output glucose range, glucose number, a change in glucose, a glucose color, or the like.

Patient data 206 may include, but is not limited to, patient identifying information (e.g., a name, birthdate, etc.), patient-entered data, and digital data indicative of historical and/or current conditions of a patient, diagnostic tests, and test results associated with the patient, medications prescribed or administered to the patient, therapies (e.g., surgeries, outpatient procedures, or the like) administered to the patient, prior and real time glucose predictions and measurements captured by wearable device 102, data stored or extracted from an electronic medical record (EMR), demographics of a patient, vital signs of a patient, notes from one or more medical appointments attended by the patient, or any combination thereof. In general, patient data 206 may be used by the systems and processes described herein when permission for using such data has been provided by the patient.

One or more processors 218 may be included in device 102. The processors 218 may be used for executing program instructions associated with apps 204, ML models 104, image analyzer 212, and/or mapping logic 208. In some embodiments, the processors 218 may include graphical processing units (GPUs) for rendering and generating graphics, images, video, audio, and/or multimedia files.

Other circuitry such as an analog-to-digital converter (ADC) 220 and a digital-to-analog converter (DAC) 222 can also be located within wearable device 102, such as co-integrated as a portion of a commonly-shared integrated circuit or integrated circuit package. The ADC 220 may convert an analog signal representation of a captured image into a digital representation of the image. The DAC 222 may convert a digital signal representation of a captured image into an analog signal for further processing.

Although the prediction system 210, image analyzer 212, mapping logic 208, and the ML models 104 are depicted as part of the wearable device 102, any or all of such functionality carried out by the prediction system 210, image analyzer 212, mapping logic 208, and/or the ML models 104 may alternatively, or additionally, be carried out by an external computing device, such as the computing device 106 in wired or wireless communication with wearable device 102. In addition, while the image analyzer 212 is depicted external to (e.g., not integrated into) ML models 104, in some embodiments, the image analyzer 212 may be integrated into the ML models 104. In addition, while the prediction system 210 is depicted internal to (e.g., integrated into) ML models 104, in some embodiments, the prediction system 210 may be external to (e.g., not integrated into) the ML models 104.

The wearable device 102 also includes or is communicatively coupled to power 240, input devices 242, and output devices 244. The power 240 may be a power source for the wearable device 102 and/or sensors 228. The power 240 may include or connect to a battery or a port for connecting the wearable device 102 to a power supply, a wall power adapter, a battery pack, or the like.

The input devices 242 may interact with memory 202, one or more processors 218, sensors 228, apps 204, image analyzer 212, prediction system 210, ML models 104, mapping logic 208, and/or patient data 206. The input devices 242 may include touchscreens, switches, buttons, toggles, and/or other hardware components located on wearable device 102. In some embodiments, the input device 242 may be external to or not integrated into the device 102, such that one or more controllers, mobile device, apps (e.g., apps 204), etc., may communicate (e.g., one or more optional antennas 224, coils, etc.) with device 102 using a wireless communications protocol. In some embodiments, the input device 242 may include, for example, a touch input device that can receive tactile user input, a microphone that can receive audible input, and the like.

The output devices 244 may interact with memory 202, one or more processors 218, sensors 228, apps 204, image analyzer 212, prediction system 210, ML models 104, mapping logic 208, and/or patient data 206. The output devices 244 may include, for example, a display (e.g., optional display 226) for visual output, a speaker for audio output, and/or haptic feedback.

In some embodiments, the wearable device 102 is a noninvasive blood glucose monitoring system that is configured to be removably coupled to a body site of a user. The wearable device 102 may include at least one optical sensor (e.g., image sensor 228) communicatively coupled to at least one light source (e.g., red-light source, near infrared light source, optional light source 232 or a light source internal to sensor 228). The optical sensor 228 may sense reflected light from the body site resulting in a captured image. The wearable device 102 may also include and be communicatively coupled to at least one processor (e.g., processor 218) which may be programmed with the techniques and algorithms described herein to programmatically analyze the captured image to determine a blood glucose estimate for the user.

Figure 3:
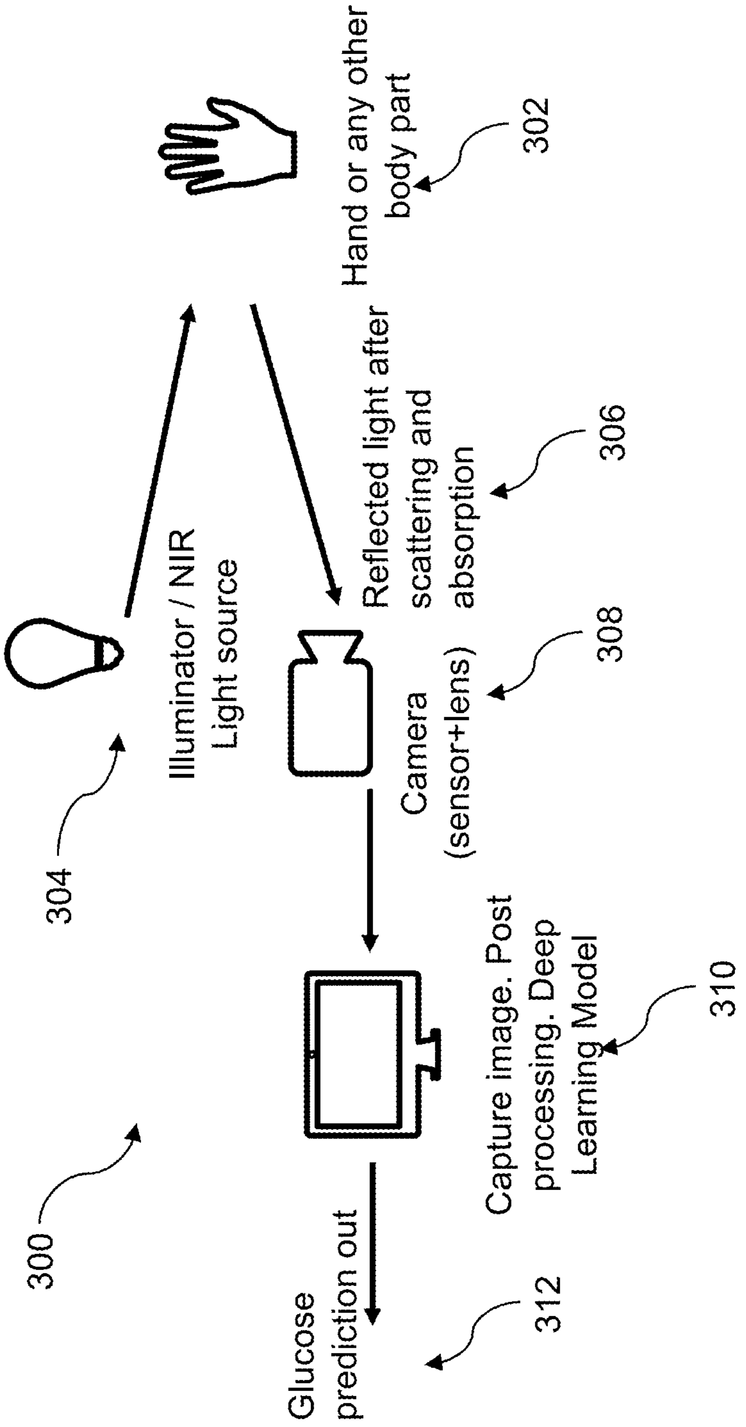
FIG. 3 is a block diagram of an example end to end system for generating noninvasive glucose assessments associated with a body site of a user.

FIG. 3 is a block diagram of an example end to end system 300 for generating noninvasive glucose assessments associated with a body site of a user. The system 300 may include the wearable device 102 (FIG. 2) placed substantially adjacent to a body site of the user, such as a volar wrist. In operation, the system 300 may illuminate (304) a body site 302 (e.g., a hand or other body part) having one or more visible venous blood vessels. The illuminating may cause (306) reflected light to scatter and absorb at the body site 302. The scattered light may be captured (308) by an image sensor 308 (e.g., image sensor 228, camera, optical sensor, etc.). The captured image may be processed (310) by one or more deep learning models (e.g., ML models 104) to generate (312) a glucose level prediction for the user associated with the body site 302.

In general, the system 300 may capture images of veins at the body site. During illumination of the body site, changes in glucose can be monitored and compared over time using system 300, as described in detail in FIG. 2. Changes in the concentration of glucose may modify the indexes of refraction of both the intracellular medium and the extracellular medium, which in turn alters the scattering properties of those media. Such changes in scattering and photon absorption in clinical measurements, as described in detail in Table 1 below, suggest a strong correlation between a reduced scattering coefficient and the concentration of glucose as determined from a blood test. As will be described in detail herein, the image recorded by an NIR image sensor 308 depicts a correlation between glucose level (as read by over-the-counter (OTC) glucose meter) and the darkness/appearance of veins and the surrounding area. The system executing on device 102 and/or system 300 may be used to detect particular glucose measurements and/or determine glucose-based or health based predictions about a user wearing device 102 based at least in part on this correlation. Thus, upon capturing one or more images of a body site, the one or more images may be stored and programmatically analyzed (i.e., using a computer system using hardware and software) to obtain a predicted output value of glucose for the user. The systems 200, 300 may learn to recognize any change in the absorption and/or scattering of NIR light within a vein to ascertain an estimated change in a glucose level in the blood of the user.

Figure 4A:
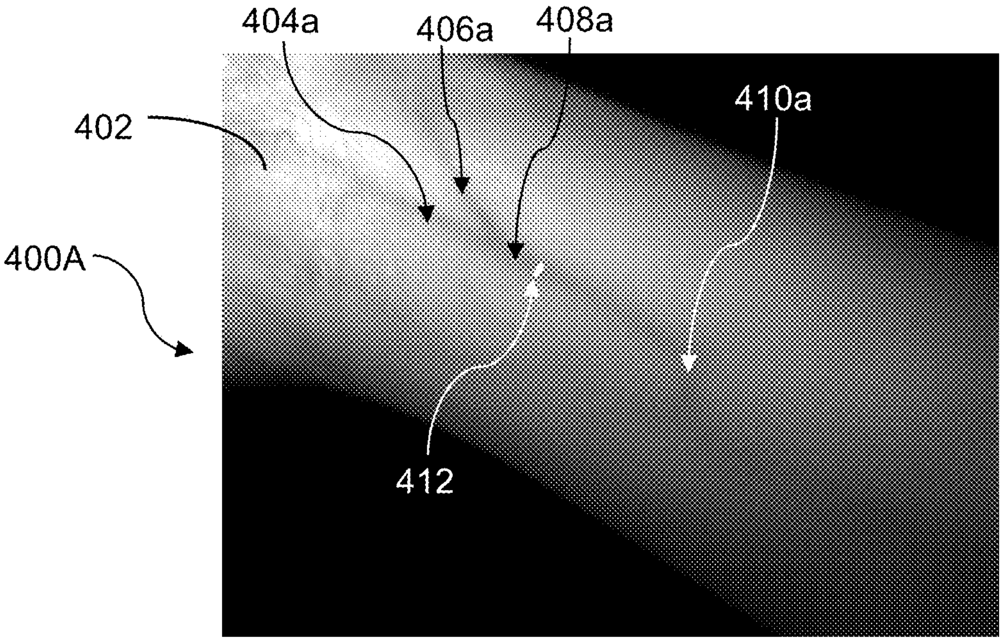
FIGS. 4A-4B illustrate photographic images depicting IR light reflecting off of a volar wrist of a user.
Figure 4B:
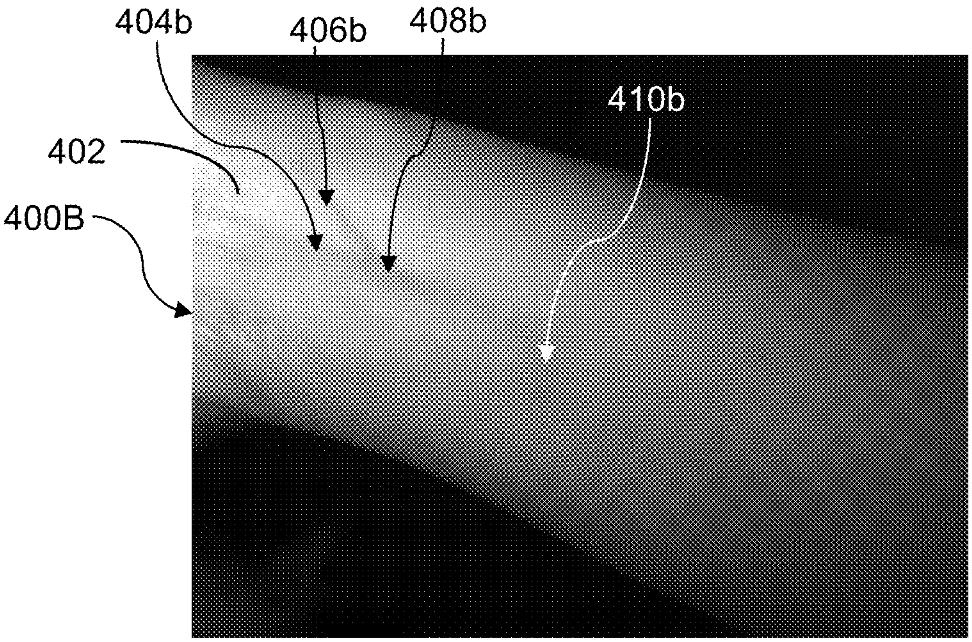

FIGS. 4A-4B illustrate photographic images 400A, 400B depicting IR light reflecting off of an arm (e.g., volar wrist 402) of a user. In this example, the volar wrist 402 may represent a body site on which device 102 may be worn. Alternatively, the volar wrist 402 may represent a body site that is placed into contact with an image sensor (e.g., image sensor 228), detector, or other element of device 102 worn on another body part in order to generate a glucose prediction/measurement for the user. While the images shown in FIGS. 4A-4B may depict a swatch of the body site that is larger than what may be captured and/or analyzed by device 102, the images represent at least portions of the arm that could be captured and analyzed by the device 102. The systems and methods described herein may of course, capture and analyze less than an entire image of a particular body part while maintaining the ability to ascertain blood glucose levels associated with less than the entire body site, and/or the ability to ascertain other physiological parameters or conditions.

FIG. 4A illustrates a photographic image 400A of a user with a glucose meter reading of about 93 mg/dL. Here, the wearable device 102 may capture at least one digital image 400A representing infrared light reflected from the arm. Here, the arm is a non-limiting example of a body site in an upper extremity of the user such that a sensor (e.g., image sensor 228) installed on the wearable device 102, for example, may capture at least one digital image of the volar wrist of the user when the wearable device 102 is worn on the wrist.

The wearable device 102 (and/or other computing device communicatively coupled to device 102) may programmatically analyze the captured digital image(s) to ascertain that digital data captured by the image sensor 228 corresponds to or is strongly suggestive of particular glucose meter reading values based on the characteristics of the reflected light. For example, the wearable device 102 (and/or other computing device communicatively coupled to device 102) may programmatically analyze the image 400A to assess blood glucose for a user. The analyzing may include segmenting, by a first ML model (e.g., ML model 104*a*) the image 400A into a plurality of regions. The regions may each include at least a portion of a venous blood vessel (e.g., vessel 404*a*, vessel 406*a*, vessel 408*a*, and/or 410*a*). The segmenting performed by ML model 104*a* may be performed to detect at least one venous blood vessel (or at least one portion of the venous blood vessel) in the image 400A, for example.

The analyzing performed by wearable device 102 (and/or other computing device communicatively coupled to device 102) may further include analyzing, by a second ML model (e.g., ML model 104*b*), a visual appearance of at least one of the identified venous blood vessels in the plurality of regions of the image. Analyzing a visual appearance may include analyzing a pixel intensity (e.g., darkness, brightness, etc.) of each venous blood vessel or portion of such a vessel represented in a given image. Each intensity level determined for a region in an image may be compared to predefined glucose data and/or patient data 206 to determine an accurate glucose level and/or glucose prediction for the user. The ML model 104*b* may use mapping logic 208 and/or prediction system 210 to determine the accurate glucose level and/or glucose prediction for the user in near real time.

For example, analyzing the visual appearance of one or more venous blood vessels in the plurality of regions includes determining an intensity level of pixels representing a portion of the venous blood vessel(s). For instance, the intensity level of pixels may represent a darkness level or brightness level that may be ascertained by processing the image 400A and determining that pixels representing the vessel portion 404*a* are at a first intensity level, while vessel portions 406*a*, 508*a*, and 410*a* are at different intensity levels. The intensity levels may be further analyzed in combination and/or with other data to generate a glucose level and/or glucose prediction for the user.

For example, additional analysis of the veins in the image 400A may be performed and combined with other analysis (e.g., determined intensity levels of particular veins, prior glucose predictions or measurements, or the like) and/or patient data 206. In some embodiments, the ML model 104*b* may also determine a dehydration level and/or an osmolality level based on one or more features of the pixels representing the portion of at least one venous blood vessel (e.g., vessel 404*a*, vessel 406*a*, vessel 408*a*, and/or 410*a*). Such features may include a blood vessel diameter 412 of the portion of one or more venous blood vessel in the image. For example, the ML model 104*b* may use the image 400A to determine a vessel diameter of any portion of vessels 404*a*-410*a*, for example. The determination of dehydration levels and/or osmolality levels may be compared to population level data, prior images associated with the user wearing device 102, and/or patient data 206 in order to determine changes in vessel diameter, vessel behavior, and/or vessel size, in general.

Another feature that the ML model 104*b* can determine is a volume of fluid in the portion of the one or more venous blood vessels in the image 400A. For example, the ML model 104*b* may analyze the fluid, particulates, and/or cross sectional areas and any associated volumes pertaining to the one or more venous blood vessels in the image 400A.

In addition, the second ML model 104*b* may also perform a classification process to classify the plurality of regions according to predefined glucose levels. For example, each of the veins in the image 400A may be classified into a particular window of glucose measurements based on a visual appearance in an image including any or all of the determined pixel intensity levels, the determined dehydration level approximations, the determined osmolality level approximations, the determined vessel diameters and related size-based parameters, and/or the determined volumes associated with at least a portion of one or more of the venous blood vessels depicted in image 400A, for example.

The wearable device 102 (and/or other computing device communicatively coupled to device 102) may then generate, based on the classifying and on the visual appearance of the at least one venous blood vessel, a blood glucose estimate for the user. That is, the wearable device 102 (and/or other computing device communicatively coupled to device 102) may utilize the pixel intensity levels, dehydration level approximations, osmolality level approximations, vessel diameters and related size-based parameters, and volumes associated with at least a portion of one or more venous blood vessels to generate a predicted glucose level and/or measurement for a user of the one or more venous blood vessels. Additional indications 250 may also be provided to a user using device 102 (and/or other computing device communicatively coupled to device 102) based on the generated predicated glucose level and/or measurement.

FIG. 4B illustrates a photographic image 400B of the same user of FIG. 4A with a glucose meter reading of about 89 mg/dL. The image 400B was captured after the user of FIG. 4A ingested a meal. The glucose level has dropped about 5 points from 93 mg/dl to 89 mg/dL. Visual changes are apparent between vessels 404*a* and 404*b*, 406*a* and 406*b*, 408*a* and 408*b*, and between vessels 410*a* and 410*b*. Namely, each vessel 404*b*, 406*b*, 408*b*, and 410*b* of FIG. 4B has less intensity, less volume, and less size than that of the veins 404*a*, 406*a*, 408*a*, and 410*a* of FIG. 4A.

The wearable device 102 (and/or other computing device communicatively coupled to device 102) may perform the same process as described in FIG. 4A (and/or FIG. 13) to ascertain parameters including, but not limited to the pixel intensity levels, dehydration level approximations, osmolality level approximations, vessel diameters and/or related size-based parameters, or volumes associated with at least a portion of vessels 404*b*, 406*b*, 408*b*, and 410*b* shown in FIG. 4B. FIG. 4B represents the vessels 404*b*, 406*b*, 408*b*, and 410*b* at a time after a meal event. The parameters may be used to determine a corresponding glucose level for the user at the time after the meal event. Classification or reclassification of outputs from ML model 104*b* may also be performed to determine an updated predicted output value (e.g., glucose level) for the user.

Figure 5A:
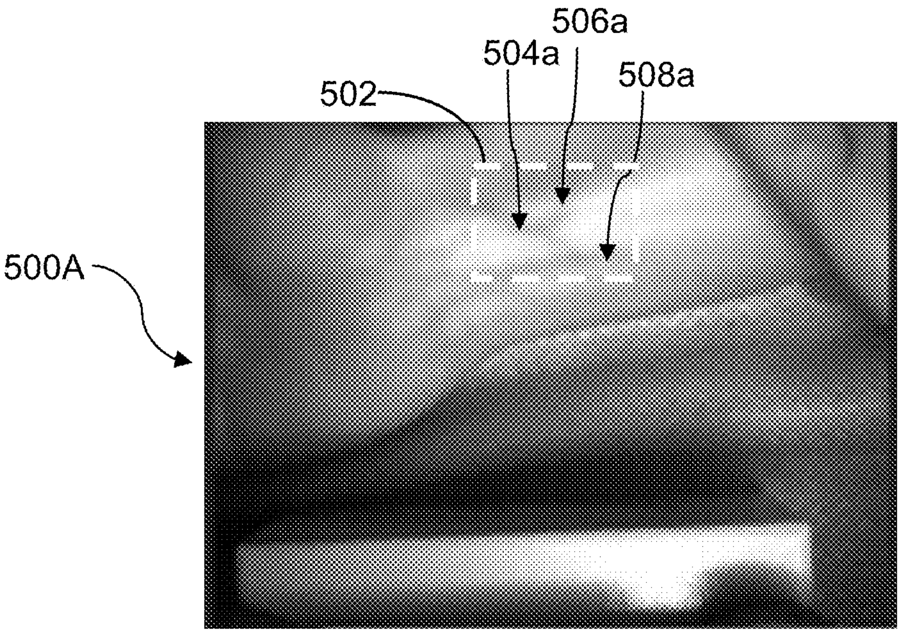
FIGS. 5A-5B illustrate photographic images depicting IR light reflecting off of a volar wrist of a user before and after an event, respectively.
Figure 5B:
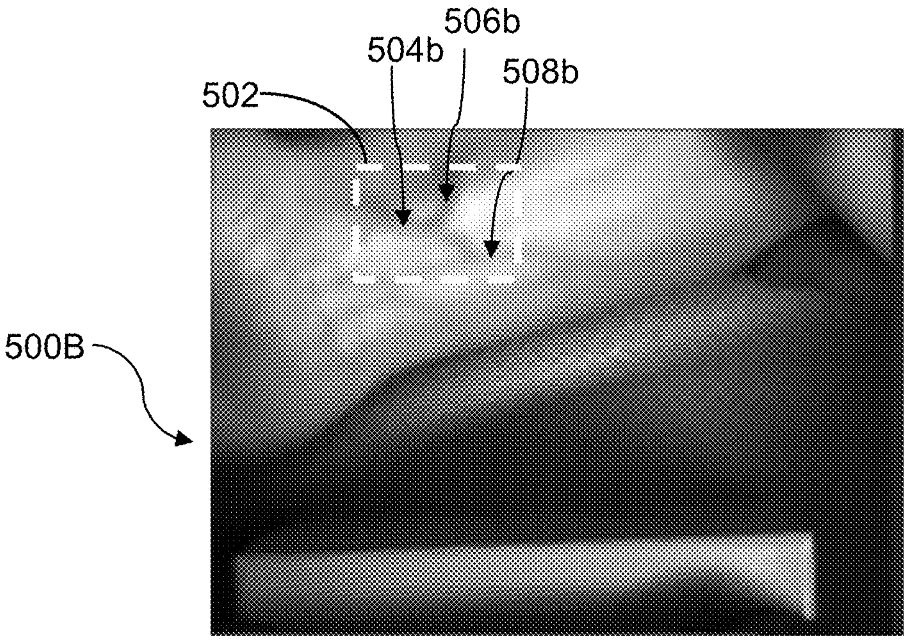

FIGS. 5A-5B illustrate photographic images 500A, 500B depicting IR light reflecting off of an arm (e.g., volar wrist body site 502) of a user before and after an event, respectively. The event described here includes ingestion of a meal, but any event that may alter blood glucose may be substituted and a blood glucose prediction/measurement can be made by wearable device 102 and/or other computing system described herein. Table 1 below indicates the event/meal and the changes in glucose levels, as measured by a glucose meter.

In this example, the body site 502 may represent a body site on which wearable device 102 may be worn. Alternatively, the body site 502 may represent a body site that is placed into contact with an image sensor (e.g., image sensor 228), detector, or other element of device 102 worn on another body part in order to generate a glucose prediction/measurement for the user. While the images shown in FIGS. 5A-5B may depict a swatch of the body site that is larger or smaller than what may be captured and/or analyzed by device 102, the images represent at least portions of the arm that could be captured and analyzed by the device 102. The systems and methods described herein may, of course, capture and analyze less than an entire image of a particular body site while maintaining the ability to ascertain blood glucose levels associated with less than the entire body site, and/or the ability to ascertain other physiological parameters or conditions.

FIG. 5A illustrates a photographic image 500A of a user with a glucose meter reading of about 97 mg/dL. The wearable device 102 (and/or other computing device communicatively coupled to device 102) may analyze the body site 502 to determine and/or predict a blood glucose level for the user wearing device 102 at a particular point in time, as described in detail herein. In this example, the analysis may be based at least in part on visually assessing a venous blood vessel 504*a*, a venous blood vessel 506*a*, and/or a venous blood vessel 508*a*. For example, the wearable device 102 may analyze a visual appearance of one or more vessels to determine a blood glucose level for the user at a point in time. For example, the wearable device 102 may analyze the visual appearance of vessel 504*a*, 506*a*, and/or 508*a* to determine a blood glucose level for the user wearing device 102. Analyzing the visual appearance of vessels 504*a*, 506*a*, and/or 508*a* may include, but is not limited to, assessing pixel intensity, osmolality, blood vessel diameter, blood vessel size, vessel length, vessel width, vessel cross-sectional area, or the like of a portion of one or more venous blood vessels 504*a*, 506*a*, and/or 508*a* in the image 500A.

FIG. 5B illustrates a photographic image 500B of a user with a glucose meter reading of about 92 mg/dL. In this example, the user wearing device 102 ingested a meal and the image 500B depicts a reading directly after ingestion of the meal. The wearable device 102 may assess the visual appearance of body site 502 and in particular, of the same vessels, shown in image 500B as vessels 504*b*, 506*b*, and 508*b*. The vessels 504*b*, 506*b*, and 508*b* are depicted with greater pixel intensity than vessels 504*a*, 506*a*, and 508*a*. In addition, vessels 504*b*, 506*b*, and 508*b* are larger (e.g., wider and longer) than vessels 504*a*, 506*a*, and 508*a*. However, the changes between image 500A and image 500B may not be apparent to the visual eye to provide a blood glucose level or measurement. As such, the wearable device 102 and in general the systems described herein may assess the images to determine and/or predict specific blood glucose levels and/or measurements such that the user may make informed decisions to maintain and/or improve blood sugar health, or the like.

Figure 6A:
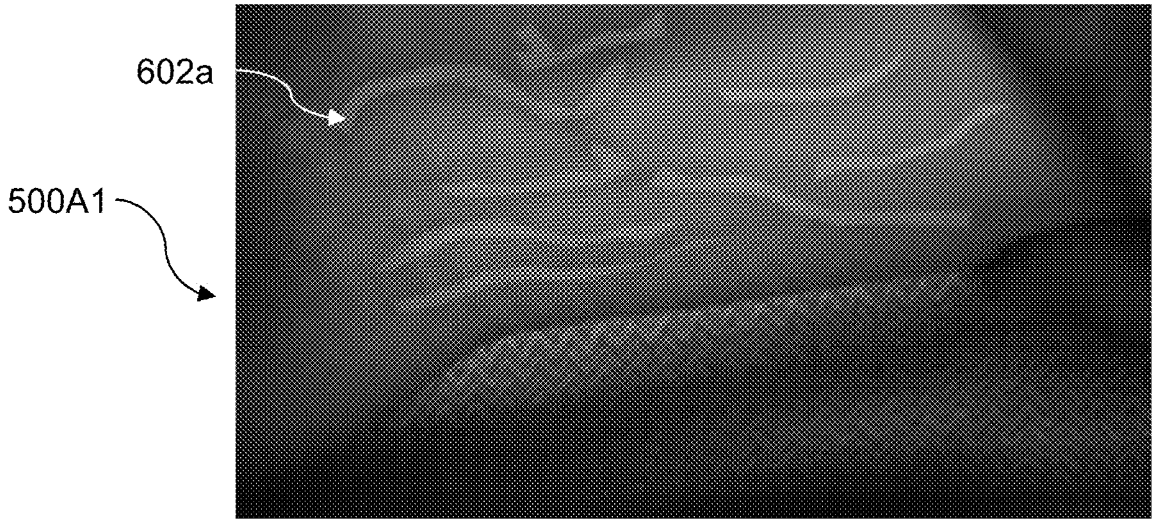
FIGS. 6A-6B illustrate photographic images of a volar wrist with mapped veins before and after an event, respectively.
Figure 6B:
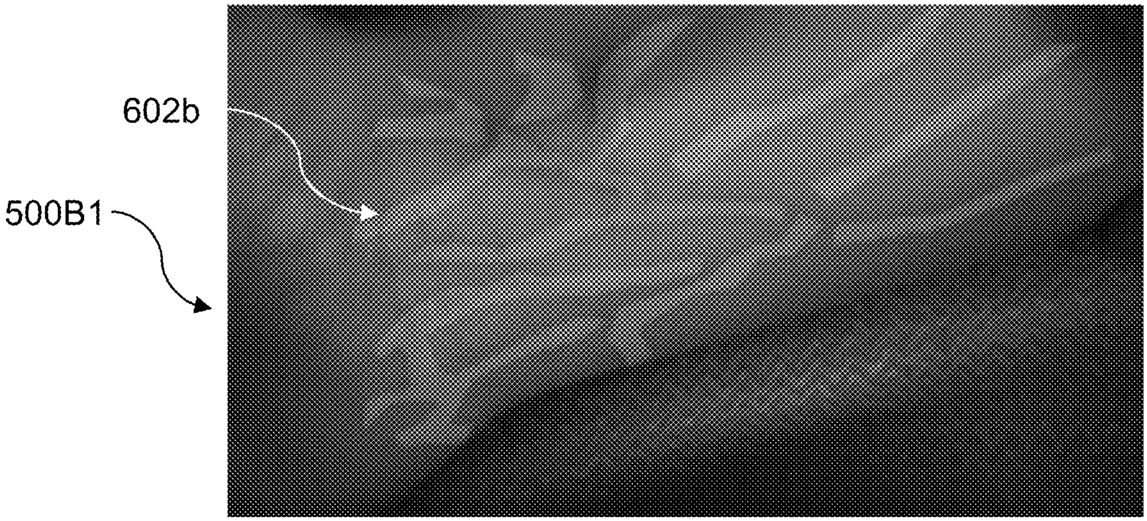

FIGS. 6A-6B illustrate photographic images of a volar wrist with mapped veins before and after an event, respectively. The user depicted in FIGS. 6A and 6B is the same user and timing as shown in FIGS. 5A and 5B, respectively. Here, the wearable device 102 and/or the systems described herein may analyze the visual appearance of venous blood vessels (and/or vessel portions) depicted in the image 500A1 to determine a first glucose measurement and/or prediction. The device 102, for example, may map particular vessels with specific measurements, overlays, and/or coordinates that may be used for future analysis of glucose for the user at a later time. For example, at a later time after an event, such as a meal.

FIG. 6B illustrates the same user of FIG. 6A after a meal event. The wearable device 102 may next analyze the visual appearance of the same venous blood vessels (and/or vessel portions) shown in image 500B1 to generate a second glucose measurement and/or prediction, which may also be marked and/or mapped with measurements, overlays (e.g., overlay 602*a*, 602*b*, etc.), and/or coordinates corresponding to changes in the visual appearance of one or more vessels.

In some embodiments, the first glucose measurement can be compared to the second glucose measurement to generate indications for the user, as described in detail herein. For example, the overlay 602*a* in image 500A1 depicts a vessel as a particular width and length while overlay 602*b* in image 500B1 differs from the width and length of overlay 602*a*. The differences can be analyzed by ML models 104 to identify specific changes in the vessel(s) over time to determine occurrences of blood glucose changes and estimates of blood glucose levels. Any number of glucose measurements and/or vessel analysis may be performed to generate additional indications or related data.

Figure 7A:
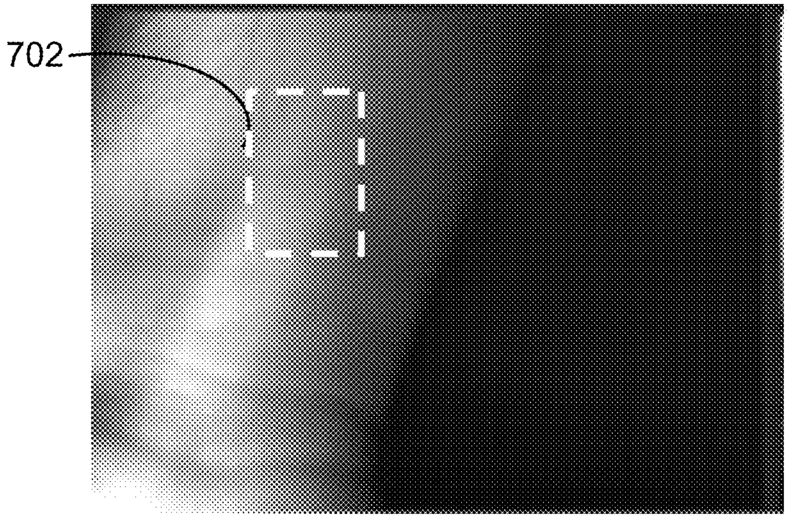
FIGS. 7A-7B illustrate photographic images of a volar wrist captured before and after a meal, respectively.
Figure 7B:
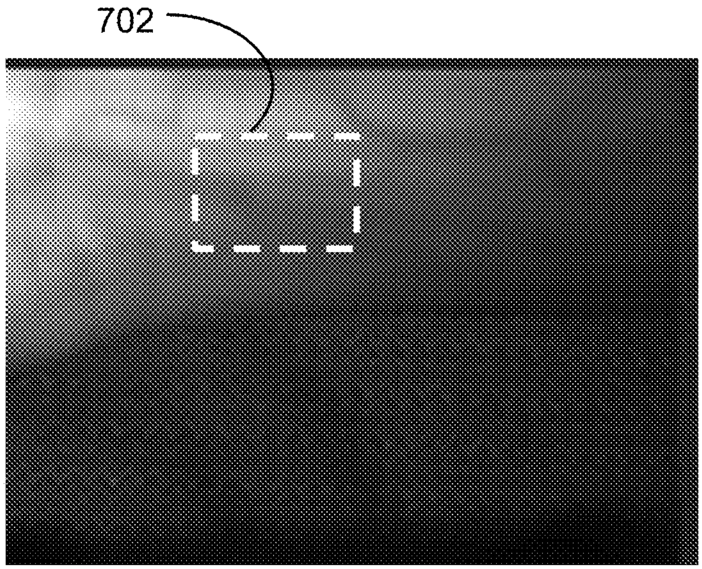

FIGS. 7A-7B illustrate photographic images of a volar wrist body site 702 captured before and after a meal, respectively. FIG. 7A illustrates the body site 702 before a meal while FIG. 7B illustrates the body site after a meal, as indicated in Table 1 below. In this example, the wearable device 102 may again analyze the change in visual appearance of vessels within body site 702 to ascertain changes in glucose over time, as described in detail herein.

Figure 8A:
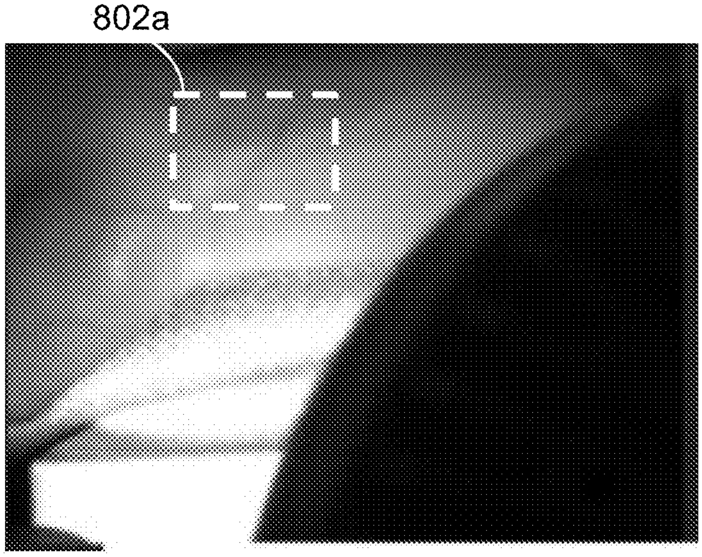
FIGS. 8A-8B illustrate photographic images of a volar wrist captured before and after a meal, respectively.
Figure 8B:
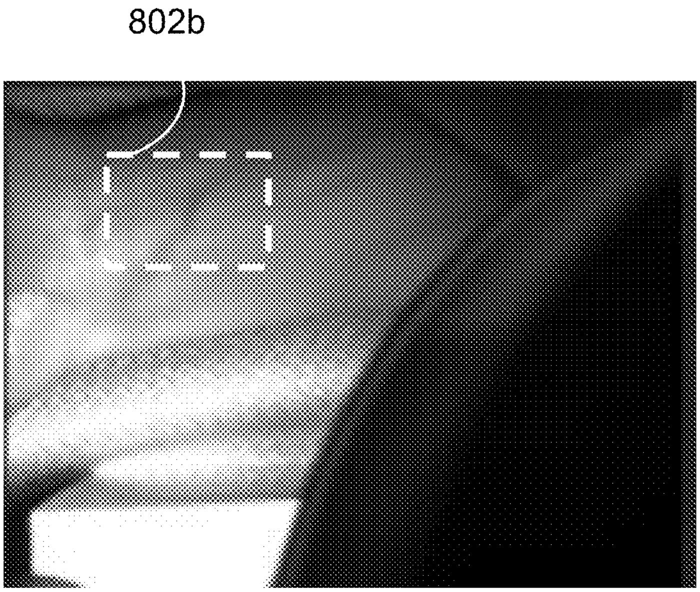

FIGS. 8A-8B illustrate photographic images of a volar wrist body site 802*a* and body site 802*b* captured before and after a meal, respectively. FIG. 8A illustrates the body site 802 before a meal while FIG. 8B illustrates the body site after a meal, as indicated in Table 1 below. In this example, the wearable device 102 may again analyze the change in visual appearance of vessels within a first body site 802*a* to ascertain changes in glucose over time by comparing to the same vessels or different vessels in a second and different body site 802*b*. For example, if wearable device 102 shifts on the body site 802*a* to body site 802*b*, assessments and predictions may still be performed by device 102 by assessing any image overlap and/or assessing additional vessels in the newest image in time (e.g., FIG. 8B).

Figure 9A:
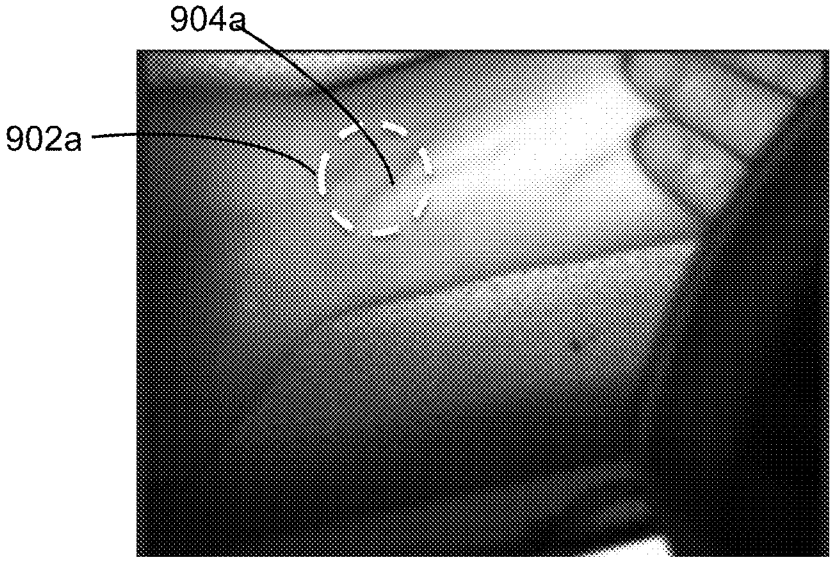
FIGS. 9A-9B illustrate photographic images of a volar wrist captured before and after a meal, respectively.
Figure 9B:
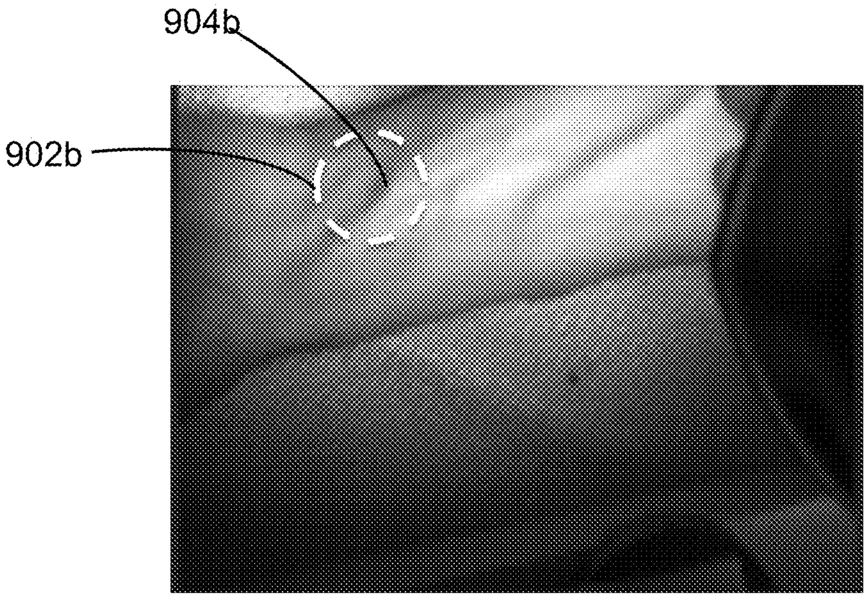

FIGS. 9A-9B illustrate photographic images of a volar wrist captured before and after a meal, respectively. FIG. 9A illustrates the body site 902 before a meal while FIG. 9B illustrates the body site after a meal, as indicated in Table 1 below. In this example, the wearable device 102 may again analyze the change in visual appearance of vessels within body site 902 to ascertain changes in glucose over time, as described in detail herein.

A vessel 904*a* is shown in both FIGS. 9A and 9B. In FIG. 9B, the vessel 904*b* is shown to have grown larger than vessel 904*a* shown in FIG. 9A. In particular, in FIG. 9B, the vessel 904*b* is shown to be bulging. This change may be detected by wearable device 102 and further analysis can be performed to identify specific changes in blood glucose that occurred between the image captures of FIG. 9A and FIG. 9B. In this example, the body site is shown as a circular shape, however, any shape or size of a capture area on a body may be used by wearable device 102.

Figure 10A:
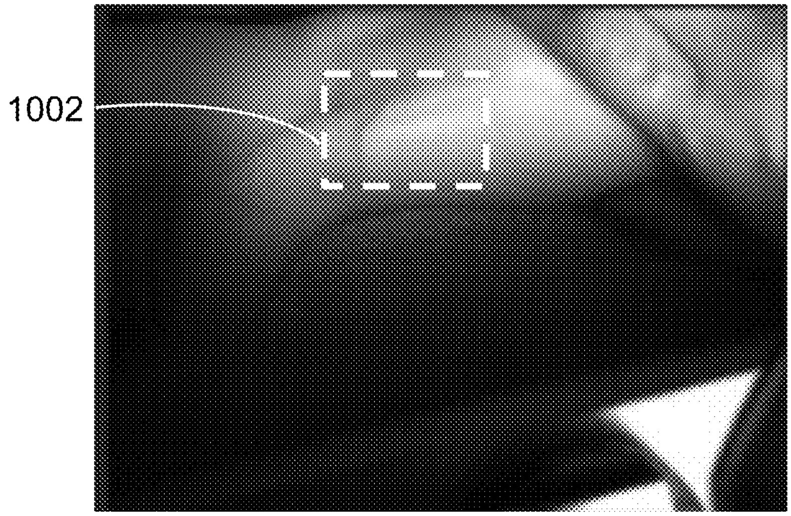
FIGS. 10A-10B illustrate photographic images of a volar wrist captured before and after a meal, respectively.
Figure 10B:
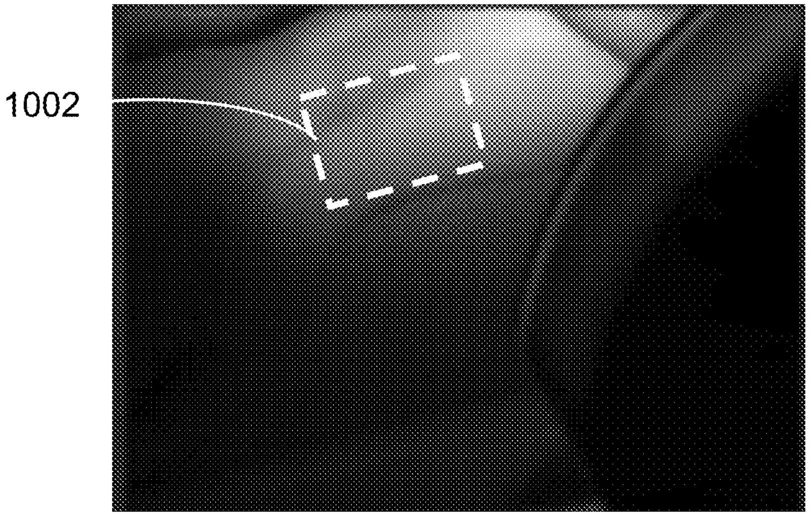

FIGS. 10A-10B illustrate photographic images of a volar wrist body site 1002 captured before and after a meal, respectively. FIG. 10A illustrates the body site 1002 before a meal while FIG. 10B illustrates the body site after a meal, as indicated in Table 1 below. In this example, the wearable device 102 may again analyze the change in visual appearance of vessels within body site 1002 to ascertain changes in glucose over time, as described in detail herein.

Figure 11A:
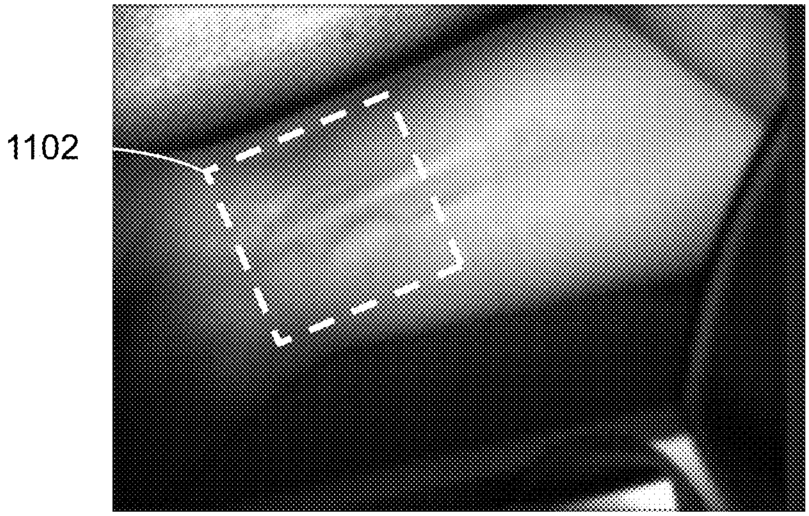
FIGS. 11A-11B illustrate photographic images of a volar wrist captured before and after a meal, respectively.
Figure 11B:
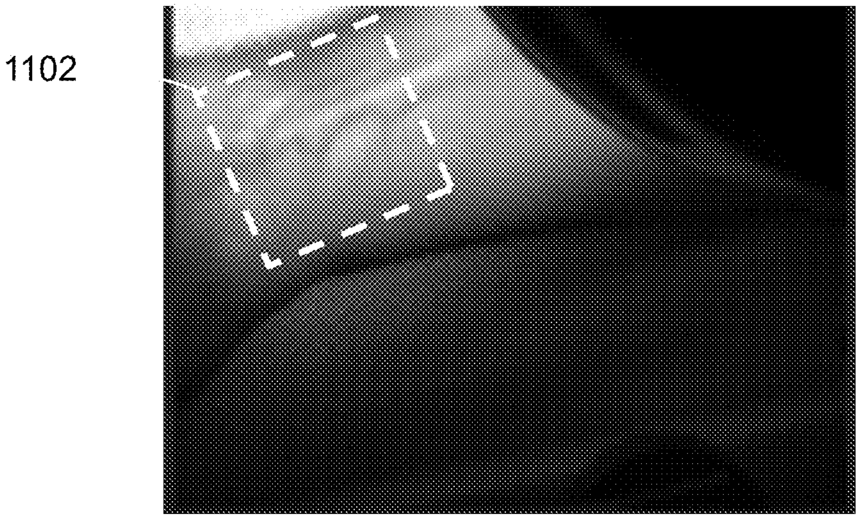

FIGS. 11A-11B illustrate photographic images of a volar wrist captured before and after a meal, respectively. FIG. 11A illustrates the body site 1102 before a meal while FIG. 11B illustrates the body site after a meal, as indicated in Table 1 below. In this example, the wearable device 102 may again analyze the change in visual appearance of vessels within body site 1102 to ascertain changes in glucose over time, as described in detail herein.

FIGS. 12A-12D illustrate example placement of an example noninvasive glucose monitoring device. The noninvasive glucose monitoring devices described herein may take any form or shape that may be fitted to a body site in which one or more venous blood vessels are visible under the skin associated with the body site. The devices of FIGS. 12A-12D may represent wearable device 102. The devices of FIGS. 12A-12D are depicted on or adjacent to a dextral or volar wrist of a user. Although the devices of FIGS. 12A-12D are depicted as a smart watch, other form factors are possible including one or more of a device integrated into a band, a watch, an adhesive strip, jewelry, a patch, clothing, or any other wearable accessory. Various shapes of the devices of FIGS. 12A-12D are depicted. However, other shapes are possible.

Figure 12A:
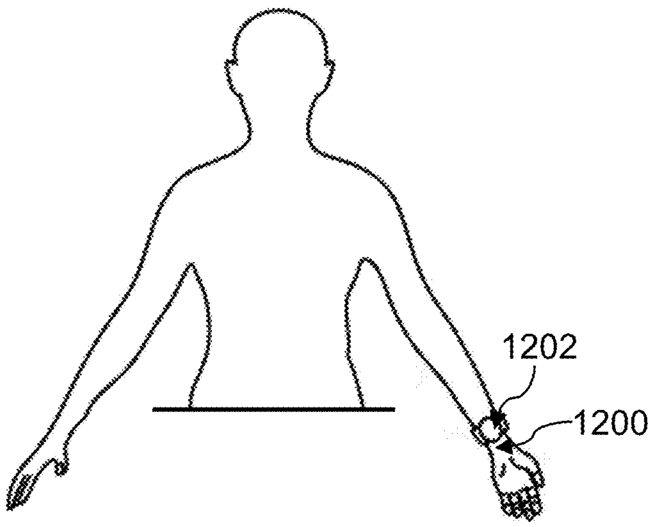
FIGS. 12A-12D illustrate example placement of an example noninvasive glucose monitoring device.

FIG. 12A illustrates an example wearable device 1200 on a volar wrist 1202 of a user. In this example, an image sensor (e.g., image sensor 228) may be coupled to (or integrated into) a base portion (not shown) of device 1200. In operation, the base portion is placed in contact with a portion of the volar wrist. The device 1200 may capture one or more images of the portion of the volar wrist 1202 of the user wearing device 1200.

Figure 12B:
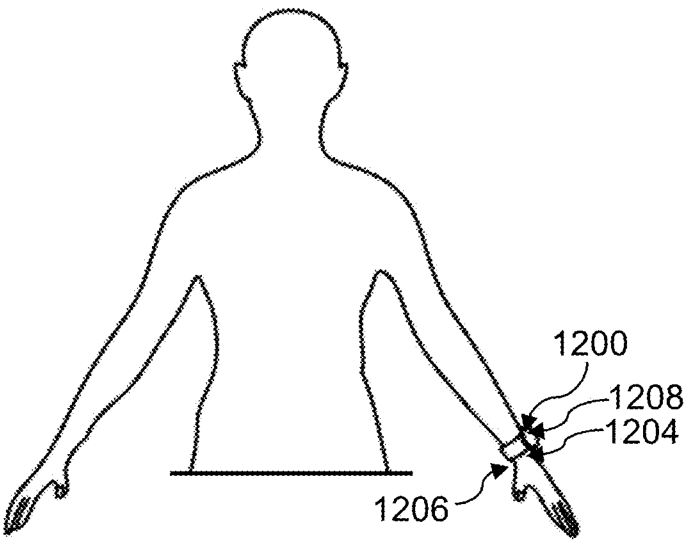
Figure 12C:
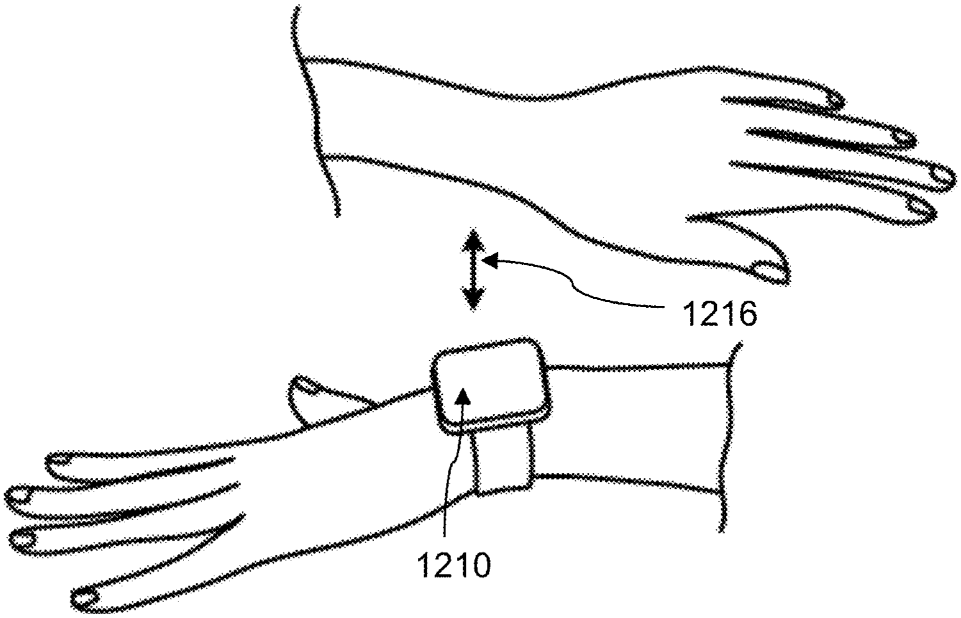
Figure 12D:
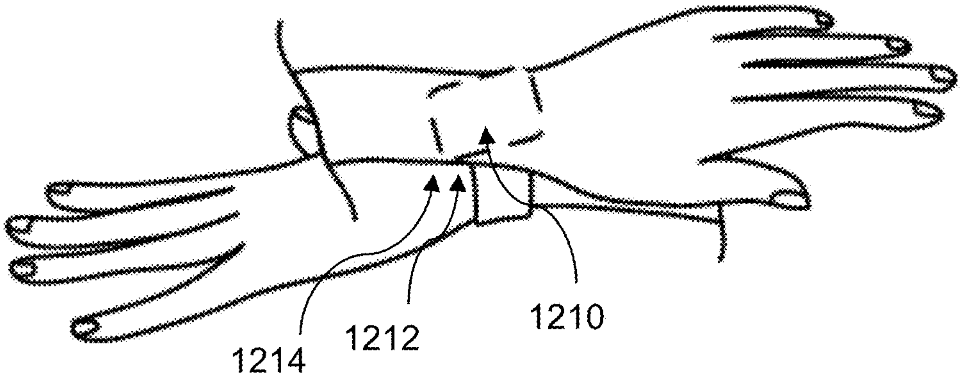

FIG. 12B illustrates the example wearable device 1200 on a dextral wrist 1204 of a user. In this example, an image sensor (e.g., image sensor 228) may be coupled to (or integrated into) a strap portion 1206 of the device 1200 to capture images of a portion of the volar wrist 1202 of the user. In some embodiments, the image sensor may instead be coupled to (or integrated into) a top portion 1208 of device 1200. In such an arrangement, images may be captured of one or more venous blood vessels in response to a user placing a body site in contact or near contact (e.g., hover) with the top portion 1208 and device 1200 detecting such contact or near contact, as shown in FIGS. 12C and 12D. In addition, such an arrangement may also allow for device 1200 to be placed in contact (or near contact) with another body portion including, but not limited to a neck, a lymph node region, or any portion of a limb, an abdominal region, or a thoracic region.

FIG. 12C illustrates an example wearable device 1210 for capturing images of body sites that are not wearing the wearable device. For example, device 1210 may include one or more image sensors (e.g., image sensors 228) on any surface of the device facing away from the skin in contact with the device. Such surfaces may include such sensors and illumination devices to capture images of body sites when the device 1210 detects a nearness or contact with a particular body site. For example, the device 1210 may be worn on a sinistral dorsal wrist 1212 with a sensor and/or light source positioned on the sinistral dorsal wrist 1212 and facing away from the sinistral dorsal wrist 1212. The user may move the dextral volar wrist 1214 toward the face of device 1210, as shown by arrow 1216. When the sensor detects that the dextral volar wrist 1214 is within a predefined range of the light source on device 1210, at least one digital image captures at least a portion of the dextral volar wrist 1214. Although FIGS. 12C-12D show the device 1210 on a sinistral wrist and detection occurring on the dextral wrist, one of skill in the art will appreciate that the device 1210 may be worn on the dextral wrist and the detection may occur on the sinistral wrist.

FIG. 12D illustrates the example wearable device 1210 of FIG. 12C capturing images of a body site that is not wearing the wearable device. In this example, the device 1210 may capture images of a body site that is placed on (or adjacent to) a sensor on device 1210.

Figure 13:
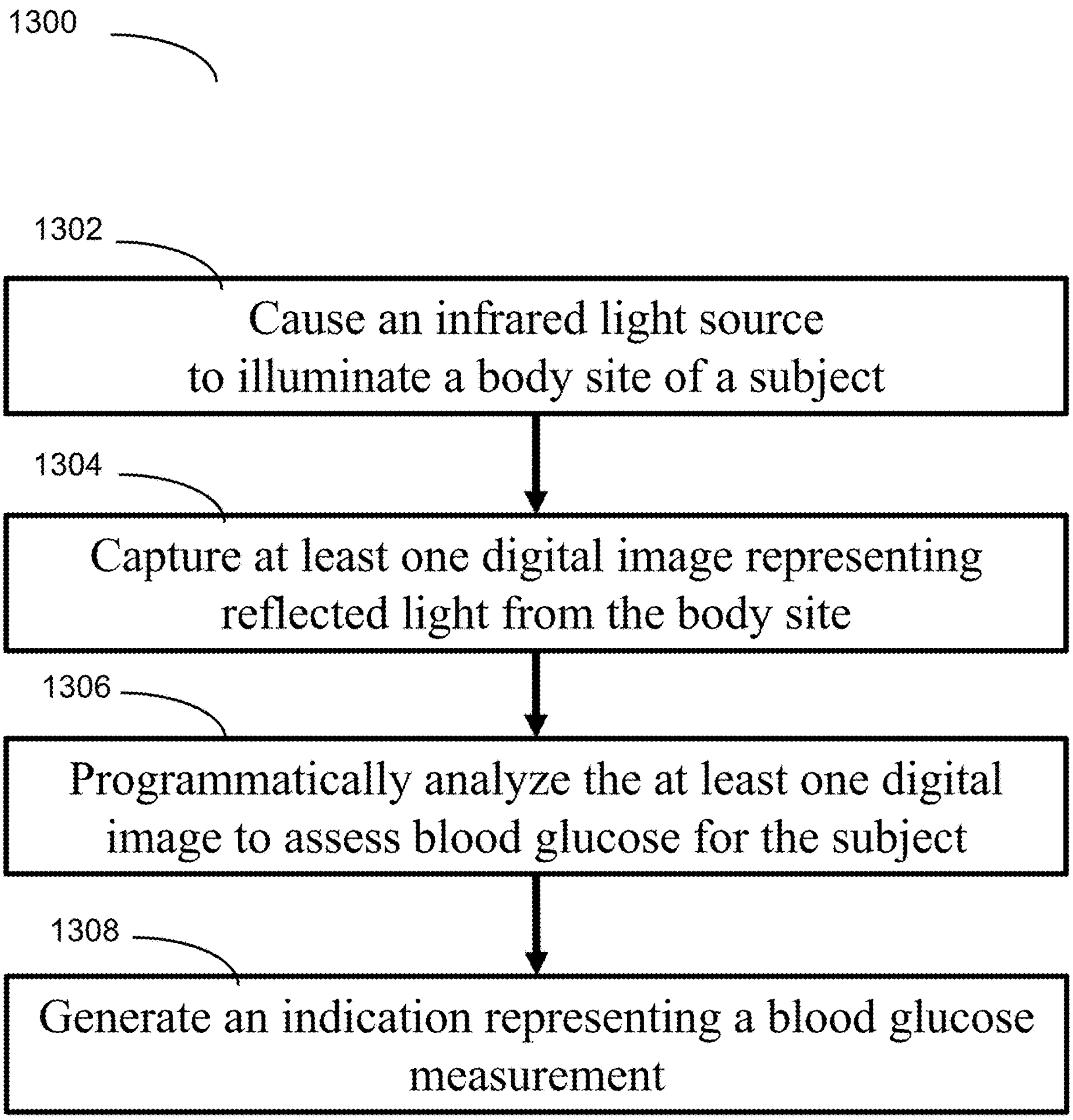
FIG. 13 is a flow diagram of an example process for performing noninvasive blood glucose monitoring of a user.

FIG. 13 is a flow diagram of an example process 1300 for performing noninvasive blood glucose monitoring of a user. The process 1300 may be performed to generate one or more predictions or measurements of a blood glucose level in a user wearing a monitoring devices, such as device 102.

The process 1300 may be executed on a processor (e.g., processors 218). The process 1300 may utilize ML models 104, prediction system 210, and mapping logic 208. Each of the ML models 104, prediction system 210, and mapping logic 208 may be in communication with one or more sensor interfaces 230 and sensors 228, apps 204, processors 1404, and/or memory 202 of device 102 to receive and process sensor signals captured at a body site of a user. The sensor signal may be obtained using device 102 or another device communicatively coupled to device 102. The process 1300 may be performed on device 102, on a companion device (e.g., mobile device), in an on-device app (e.g., app 204), in a third-party app, or on the cloud, or the like.

At block 1302, the process 1300 includes causing a light source to illuminate a body site of a subject. For example, the optional light source 232 or a light source of image sensor 228 may receive instructions to illuminate the body site of a user. The instructions may be provided by a program executing on wearable device 102 or executing on a device communicatively coupled to device 102. The illumination may provide NIR light to the body site.

At block 1304, the process 1300 includes capturing at least one digital image representing reflected light from the body site. For example, the image sensor 228 may capture one or more images (e.g., image signals, digital images, light reflections, digital video, one or more sequences of image frames, etc.) of one or more venous blood vessels (or venous blood vessel portions) viewable on the surface of skin at the body site. In operation, the image sensor 228 may be installed on device 102 in an arrangement to capture an image/image signal of at least one venous blood vessel portion in the image capture. The portion can be used to perform the analysis of glucose levels for the user.

At block 1306, the process 1300 includes programmatically analyzing the at least one image to assess blood glucose for the subject. For example, the wearable device 102 (and/or other computing device communicatively coupled to device 102) may programmatically analyze the captured image(s) to determine a blood glucose level or measurement for the user based at least in part on the characteristics of the reflected light. For example, the wearable device 102 (and/or other computing device communicatively coupled to device 102) may programmatically analyze a captured image to assess blood glucose levels.

In some embodiments, programmatically analyzing the at least one digital image may be performed to compare the at least one digital image to any number of previously captured prior digital images of the body site as a way to ascertain changes in blood glucose levels of the user in response to an event. For example, the analysis of digital images captured by device 102 can be assessed and compared over time to determine past behavior of glucose levels for a specific user and infer future behavior of the glucose levels for the specific user.

At block 1308, the process 1300 includes generating an indication (e.g., indications 250) representing the blood glucose estimate. For example, the analysis described herein may result in an output that is a blood glucose estimate and/or related prediction representing a glucose level for the user of the body site. The output may be further analyzed to generate an indication that may be communicated to an app, the user, or other user with permissions to receive glucose data about the user under test. The indication may be textual, audial, visual (e.g., messages, notifiers, animations, graphical content, image based content, etc.), or a combination thereof, as described in further detail herein.

In some embodiments, the blood glucose estimate may be expressed as a (a) range of values or as (b) a category in a plurality of categories. For example, each class of image features/glucose levels may include a class size of about 5 mg/dL. A total range of clinical significance may be about 54 mg/dL to about 250 mg/dL. In such an example, the outputs of the ML classifier may include (i) about 54 mg/dL to about 59 mg/dL, (ii) about 60 mg/dL to about 65 mg/dL (iii) about 66 mg/dL to about 71 mg/dL, etc. The total number of such output classes may be about 33 classes. In the event that class sizes are configured to be greater than 5 mg/dL, fewer total output classes may be used. Modifying the class size may be used to increase the accuracy of the ML models described herein.

In some embodiments, a classification is not performed and instead a machine learning regression model is utilized by the ML models described herein. In such an example, each integer value in the range of about 54 mg/dL to about 250 mg/dL may represent a potential output of the machine learning regression model.

In some embodiments, the classification may include classifying image features/glucose levels according to color coding. The color coding may pertain to ranges as described elsewhere herein. However, this color coding may ensure that a user may understand a glucose level by recognizing colors that familiarly indicate low glucose, high glucose, average glucose, etc. For example, green may indicate that blood glucose levels are average or good such that no action is being asked of the user. Orange or red may indicate that glucose is becoming higher than average (e.g., orange) or becoming dangerously high or low (e.g., red), which may signal to the user to perform particular actions to correct the glucose level.

In some embodiments, the classification may include classifying image features/glucose levels according to an application-specific unit or scale. For example, the classification may include classifying a particular subject into a particular glycemic level over a predefined number of hours or days.

In some embodiments, the classification may include outputting a change in glucose value. Such a classification may avoid calibration steps that may otherwise be used. For example, a change in glucose after exercise may be −5 mg/dL. Further, for example, a change in glucose after sleeping (e.g., a fasting state) may be −15 mg/dL.

In some embodiments, the indication representing the blood glucose estimate and/or related prediction may include application data (e.g., for or from one or more app(s) 204). The application data may be arranged in a way to present the blood glucose measurements and/or related predictions to the user in one or more of: an email, a display screen, a text message, an audio entry, and a visual indicator (e.g., indicator(s) 250) within a computing device or wearable device associated with the subject or a care provider of the subject.

In some embodiments, the indication representing the blood glucose estimate and/or related prediction may be provided as a notification to one or more interested parties who have (a) indicated an interest in receiving notifications and (b) are approved by the subject. For example, the indication may be associated with one or more rules for sharing indications about a particular user in which the indication pertains.

In some embodiments, a predicted output value or indication 250 about a glucose level for a user may be expressed as a specific number or a range or category. The predicted output value may also be expressed as a measurement or estimate that is estimated to be accurate within a predefined margin of error. The predicted output value may be, at least in part, expressed using one or more colors and/or audio cues within an app 204, for example, to help inform a user, particularly in ways that can reach audiences of varying ages (e.g., children, the elderly, care providers, etc.) and abilities (e.g., hearing or visually impaired). For example, a certain color and/or audio cue may correspond with a certain category or level of glucose in the blood. In this way, if a user has a difficult time interpreting a numerical value, the use of color on the display and/or audio cue may assist in informing the user about a determined glucose level or prediction.

With respect to block 1306, in some embodiments, the analyzing may include segmenting, by a first ML model (e.g., ML model 104*a*) one or more images into a plurality of regions. The regions may each include at least a portion of a venous blood vessel (e.g., vessel 404*a*, vessel 406*a*, vessel 408*a*, and/or 410*a* of FIG. 4A). The segmenting performed by ML model 104*a* may be performed to detect at least one venous blood vessel (or at least a portion of one or more venous blood vessels).

The analyzing performed by wearable device 102 (and/or other computing device communicatively coupled to device 102) may further include analyzing, by a second ML model (e.g., ML model 104*b*), a visual appearance of at least one of the identified venous blood vessels in the plurality of regions of the image. Analyzing a visual appearance may include analyzing a pixel intensity (e.g., darkness, brightness, etc.) of each venous blood vessel or portion of such a vessel represented in a given image. Each intensity level determined for a region in an image may be compared to predefined glucose data and/or patient data 206 to determine a glucose level estimate (e.g., a glucose prediction) for the user. The ML model 104*b* may use mapping logic 208 and/or prediction system 210 to determine the glucose level estimate for the user in near real time.

For example, analyzing the visual appearance of one or more venous blood vessels in the plurality of regions includes determining an intensity level of pixels representing a portion of the venous blood vessel(s). For instance, the intensity level of pixels may represent a darkness level or brightness level that may be ascertained by processing the image 400A and determining that pixels representing a first vessel (or vessel portion) are at a first intensity level, while additional vessels (or vessel portions) are at various different intensity levels. The combination of intensity levels of each vessel and/or vessel portion may be further analyzed with other data to generate a glucose level estimate for the user.

In some embodiments, additional analysis of the veins in one or more captured images may be performed and combined with other analysis (e.g., the determined intensity levels of particular veins, prior glucose predictions or measurements, or the like) and/or patient data 206. For example, the ML model 104*b* may also determine a dehydration level and/or an osmolality level based on one or more features of the pixels representing the portion of at least one venous blood vessel. Such features may include a blood vessel diameter or size of a portion of one or more venous blood vessel in the one or more images. The determination of dehydration levels and/or osmolality levels may be compared to population level data, prior images associated with the user wearing device 102, and/or patient data 206 in order to determine changes in vessel diameter, vessel behavior, and/or vessel size. In some embodiments, the vessel size may include length, width, cross-sectional area, etc.

Another feature that the ML model 104*b* can determine is a volume of fluid in the portion of the one or more venous blood vessels in one or more image captured by device 102. For example, the ML model 104*b* may analyze the fluid, particulates, and/or cross-sectional areas and any associated volumes pertaining to the one or more venous blood vessels in one or more of the captured images.

In addition, the second ML model 104*b* may also perform a classification process to classify the plurality of regions according to predefined glucose levels. For example, each of the veins or vein portions in one or more captured images may be classified into a particular window of glucose measurements based on a visual appearance in an image including any or all of the determined pixel intensity levels, the determined dehydration level approximations, the determined osmolality level approximations, the determined vessel diameters and related size-based parameters, and/or the determined volumes associated with at least a portion of one or more of the venous blood vessels depicted in the one or more captured images.

The wearable device 102 (and/or other computing device communicatively coupled to device 102) may then generate, based on the classifying and on the visual appearance of the at least one vein, a blood glucose estimate for the user. That is, the wearable device 102 (and/or other computing device communicatively coupled to device 102) may utilize the pixel intensity levels, dehydration level approximations, osmolality level approximations, vessel diameters and related size-based parameters, and volumes associated with at least a portion of one or more veins (or vein portions) to generate a predicted glucose level estimate (and/or related predictions or measurements) for a user of the one or more veins or vein portions.

In some embodiments, the process 1300 may further include monitoring the subject over time. For example, the process 1300 may include monitoring the subject with wearable device 102 by repeating the illumination of the body site, repeating the capturing of digital images to capture additional digital images of the venous body site during the monitoring process, and performing additional programmatical analysis of the additional digital images to determine any number of additional blood glucose estimates or predictions for the user. The ML models 104 may perform the additional programmatical analysis to generate a visual mapping depicting the blood glucose estimate and the additional blood glucose estimates in a time-based graph (e.g., shown in FIG. 1 by computing device 106) and as described in additional detail throughout this disclosure.

In some embodiments, the monitoring may be performed continually. In some embodiments, the monitoring may be performed intermittently. In some embodiments, the monitoring may be performed according to a predefined schedule. In some embodiments, the monitoring may be performed according to a predefined event schedule. In some embodiments, the monitoring may be performed on-demand.

In some embodiments, the process 1300 may further include generating a first set of measurements associated with features of the at least one venous blood vessel detected in the at least one digital image at a first point in time. For example, the ML model 104*b* may assess segmented images of a first set of measurements associated with veins or vein portions in the at least one digital image at time (t). Next, the process 1300 may include generating a second set of measurements for at least one image of the additional digital images corresponding to the same body site in the at least one digital image. The second set of measurements may correspond to the features of the at least one venous blood vessel at a second point in time. Next, the ML model 104*b* may compare the first set of measurements to the second set of measurements to determine an updated glucose measurement for the user. Additional assessments and/or predictions may also be performed by ML model 104*b* and such assessments and/or predictions may be provided as output as described in detail throughout this disclosure.

In some embodiments, the process 1300 may be carried out on a computing device in communication with the wearable device 102. For example, the process 1300 may be executed on one or more processors of a smart phone, a smart watch, a mobile gaming device, a laptop computer, a desktop computer, a cloud hosted computer, or the like.

In such an arrangement, the method 1300 may include performing noninvasive blood glucose monitoring of a user. The process may include causing a light source to illuminate a body site of the user, capturing at least one digital image representing reflected light from the body site, programmatically analyzing the at least one digital image by the at least one processor to assess blood glucose for the user. The analyzing may include receiving a segmentation output from a first machine learning model. The segmentation output may include identified venous blood vessel portions in the at least one digital image and image segments representing a plurality of regions of the at least one digital image. The analyzing may further include receiving analysis output from a second machine learning model. The analysis output may include identification of one or more portions in the segments of the at least one digital image and a visual appearance assessment of the portions of the venous blood vessel in the plurality of regions. The analysis may further include receiving, based on the segmentation output and the analysis output, a blood glucose estimate for the user. The process 1300 may include generating an indication representing the blood glucose estimate.

In some embodiments, the first machine learning model and the second machine learning model are accessed on a cloud-based computing device (e.g., cloud servers executing ML models 104) by a noninvasive blood glucose monitor (e.g., wearable device 102) that may monitor the user. For example, process 1300 may be performed on a cloud-based computing device.

In some embodiments, the visual appearance assessment of the portions of the venous blood vessel in the plurality of regions includes determining an intensity level of pixels representing a portion of the at least one venous blood vessel in the at least one digital image and determining an osmolality level based on one or more features of the pixels representing the portion of the at least one venous blood vessel in the at least one digital image. Such features may include a determined vessel diameter of the portion of the at least one venous blood vessel in the at least one digital image and/or a determined volume of fluid in the portion of the at least one venous blood vessel in the at least one digital image.

In some embodiments, the process 1300 may include monitoring, the subject over time, to capture a plurality of additional images, programmatically analyzing the additional images to determine a plurality of additional blood glucose estimates for the subject, and generating a visual mapping depicting the blood glucose estimate and the plurality of additional blood glucose estimates in a time-based graph.

EXTENSIONS AND FURTHER EMBODIMENTS

In some embodiments, the image sensor 228 may exchange data (such as captured image and video) over a wireless network or Bluetooth connection to a computer system designed to perform analysis on the image (and potentially video) data captured by the image sensor 228. In some embodiments, that data may be exchanged over a physical link; for example, the software responsible for performing analysis on the captured digital images/videos may reside and execute in the same physical structure as the image sensor 228.

In some embodiments, the light source 232, image sensor 228, and computer system (e.g., computer system 1400 or computing device 106) for running image analysis may be designed with a convenient form factor adaptable for use in a convenient location, such as the kitchen, car, bathroom, or office. Embodiments may also be incorporated into wearable technology, such as wearable device 102, or another device that may be incorporated into clothing or otherwise worn/carried by a human. Embodiments may also be incorporated into mobile phones and other portable devices.

In embodiments where the accuracy of the glucose readings has exceeded a specified threshold, then an alert can be issued to the user and potential other interested/approved parties (such as a care provider or family member) when a glucose level exceeds a predefined threshold of a predefined normal range for the user.

Embodiments may be used to provide useful information to a user pertaining to user health and wellness on a range of topics, including but not limited to (a) the location of veins in the body, (b) the size, diameter, and/or width of veins in the body, (c) the propensity of change in glucose levels after certain events, such as one or more of: a meal, a fast, a physical stressor, an emotional stressor, a sleep event (e.g., excess sleep, sleep deprivation, exhaustion, etc.), a time of day, and a change in estrogen (d) an indirect measurement of dehydration and/or osmolality by measuring water content in the blood or directly measuring osmolality, (e) measuring the fat content in the blood carried by the veins, and/or (f) information about any substance in blood that shows a specific spectral signature in the wavelength range from about 700 nm to about 2500 nm.

Example 1

Table 1 below includes data results from an experiment that compared readings generated by a glucometer and readings generated by image sensors. In the experiment, pre-meal and post-meal readings were taken from 33 non-diabetic individuals with consent. Post-meal readings from all participants were taken at exactly 1.5 hours after commencement of a meal. In this example, five different optical sensors were evaluated including Shortwave infrared (SWIR) cameras used with different light sources in the about 1050 nm to about 1550 nm. The Abbott FREESTYLE LITE finger prick glucose meter was used as a reference. The total number of data points collected was 408. Images associated with the experiment are shown in FIG. 5A, FIG. 5B, FIG. 7A, FIG. 7B, FIG. 8A, FIG. 8B, FIG. 9A, FIG. 9B, FIG. 10A, FIG. 10B, FIG. 11A, and FIG. 11B.

TABLE 1

Data Results

| User #ID | Age Range | Gender | Race/ Ethnicity | Before meal gluco-meter reading (mg/dL) | After meal gluco-meter reading (mg/dL) | Delta mg/dL | Meal | (NIR) outputs |
|---|---|---|---|---|---|---|---|---|
| 1 | 40-44 | M | Indian | 82 | 132 | 50 | Indian white naan and paneer (Indian cheese) | FIG. 7A, 7B |
| 11 | 40-44 | M | Chinese | 98 | 110 | 12 | unknown | FIG. 5A, 5B |
| 12 | 55-59 | F | Vietnamese | 96 | 96 | 0 | corn chips, cheese pizza, salsa, a little cabernet sauvignon | FIG. 8A, 8B |
| 21 | 40-44 | F | Indian | 97 | 92 | −5 | 2 slices of veggie pizza and a cup of Indian chai | FIG. 10A, 10B |
| 26 | 50-54 | M | Indian | 71 | 121 | 50 | 3 wheat rotis, 3/4 cup okra, potato curry, 1/2 cup mango pulp, 1 cup spinach, cucumber, bell pepper salad (no dressing). | FIG. 9A, 9B |
| 33 | 70-74 | F | Indian | 91 | 108 | 17 | Wheat roti, curry (greens, cauliflower), nuts, cream | FIG. 11A, 11B |

Data proved that the NIR optical sensor technology is independent of gender, race, and age. It proved about 56% correlation between the delta in finger prick reading and the observed changes by the embodiments described herein. The described embodiments may provide an advantage of detecting possible errors in the conventional glucose meter.

Figure 14:
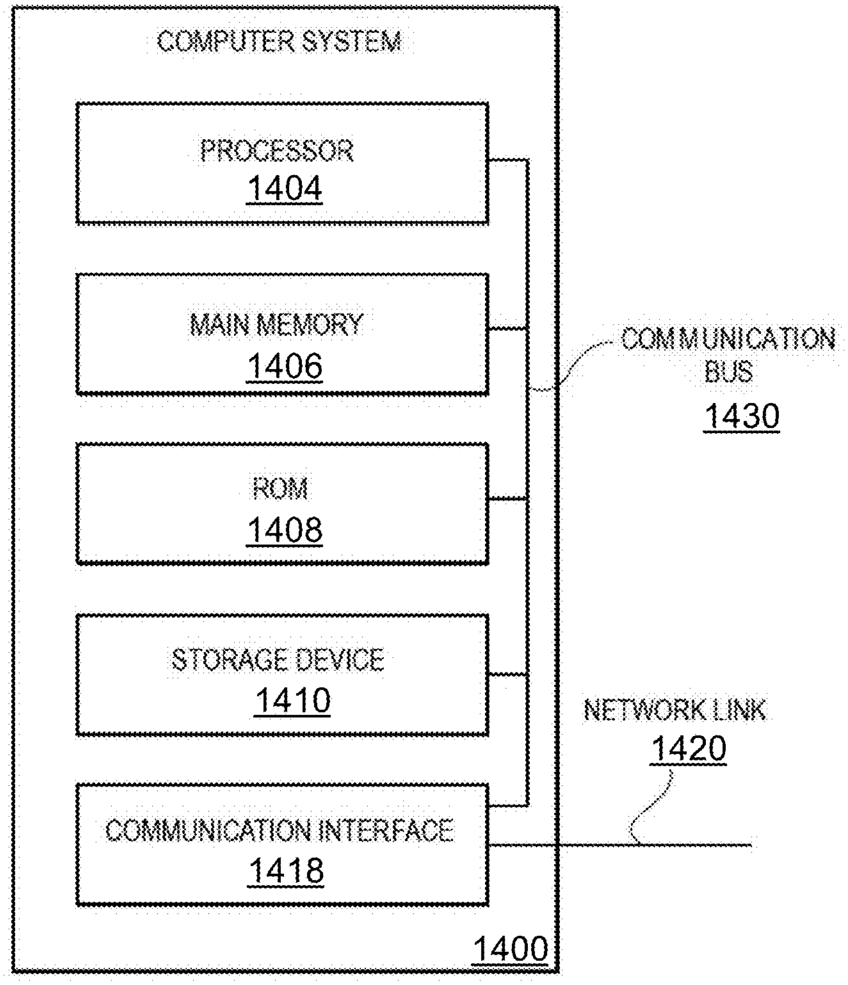
FIG. 14 is a block diagram of an example computing system for performing noninvasive blood glucose monitoring of a user and monitoring well-being and/or glucose.

FIG. 14 is a block diagram of an example computing system for performing noninvasive blood glucose monitoring of a user and monitoring well-being and/or glucose. The computer system 1400 which may control the operation of one or more of a light source (e.g., an IR light source, red-light source, light source 232), a digital camera (e.g., image sensor 228), and a software (e.g., within memory 202) for programmatically analyzing images/reflected light captured by the digital camera to capture or generate blood glucose estimates, predictions, and associated data. In some embodiments, system 1400 may represent a portion of the hardware of the wearable device 102.

In some embodiments, computer system 1400 includes one or more processors 1404 (e.g., processors 218), main memory 1406 (e.g., memory 202), ROM 1408, storage device 1410, and communication interface 1418. The at least one processor 1404 may process information. Memory 1406, such as a random-access memory (RAM) or other dynamic storage device, may function to store information and instructions to be executed by processors 1404. Main memory 1406 also may be used for storing temporary variables or other intermediate information during execution of instructions to be executed by processor 1404. Computer system 1400 further includes a read only memory (ROM) 1408 or other static storage device for storing static information and instructions for processor 1404. A storage device 1410, such as a magnetic disk or optical disk, is provided for storing information and instructions.

The described embodiments are related to the use of computer system 1400 for implementing the techniques described herein. In some embodiments, such techniques are performed by computer system 1400 in response to processor 1404 executing one or more sequences of one or more instructions contained in main memory 1406. Such instructions may be read into main memory 1406 from another machine-readable medium, such as storage device 1410. Execution of the sequences of instructions contained in main memory 1406 causes processor 1404 to perform the process steps described herein. In some embodiments, hard-wired circuitry may be used in place of or in combination with software instructions to implement particular embodiments. Thus, the described embodiments are not limited to any specific combination of hardware circuitry and software.

The term "non-transitory computer-readable storage medium" as used herein refers to any tangible medium that participates in storing instructions which may be provided to processor 1404 for execution. Non-limiting, illustrative examples of non-transitory machine-readable media include, for example, a solid-state device, a floppy disk, a flexible disk, hard disk, magnetic tape, or any other magnetic medium, a CD-ROM, any other optical medium, a RAM, a PROM, and EPROM, a FLASH-EPROM, any other memory chip or cartridge, or any other medium from which a computer can read.

Various forms of non-transitory computer-readable media may be involved in carrying one or more sequences of one or more instructions to processor 1404 for execution. For example, the instructions may initially be carried on a magnetic disk of a remote computer. The remote computer can load the instructions into its dynamic memory and send the instructions over a network link 1420 to computer system 1400.

Communication interface 1418 provides a two-way data communication coupling to a network link 1420 that is connected to a local network. For example, communication interface 1418 may be an integrated services digital network (ISDN) card or a modem to provide a data communication connection to a corresponding type of telephone line. As another example, communication interface 1418 may be a local area network (LAN) card to provide a data communication connection to a compatible LAN. Wireless links may also be implemented. In any such implementation, communication interface 1418 sends and receives electrical, electromagnetic, or optical signals that carry digital data streams representing various types of information.

Network link 1420 typically provides data communication through one or more networks to other data devices. For example, network link 1420 may provide a connection through a local network to a host computer, a mobile phone, or to data equipment operated by an Internet Service Provider (ISP).

Computer system 1400 can send messages and receive data, including program code, through the network(s), network link 1420 and communication interface 1418. For example, a server might transmit a requested code for an application program through the Internet, a local ISP, a local network, subsequently to communication interface 1418. The received code may be executed by processor 1404 as it is received, and/or stored in storage device 1410, or other non-volatile storage for later execution.

The term "about" or "approximately," when used before a numerical designation or range (e.g., to define a length or pressure), indicates approximations which may vary by (+) or (−) 5%, 1% or 0.1%. All numerical ranges provided herein are inclusive of the stated start and end numbers. The term "substantially" indicates mostly (i.e., greater than 50%) or essentially all of a device, substance, or composition.

As used herein, the term "comprising" or "comprises" is intended to mean that the devices, systems, and methods include the recited elements, and may additionally include any other elements. "Consisting essentially of" shall mean that the devices, systems, and methods include the recited elements and exclude other elements of essential significance to the combination for the stated purpose. Thus, a system or method consisting essentially of the elements as defined herein would not exclude other materials, features, or steps that do not materially affect the basic and novel characteristic(s) of the claimed disclosure. "Consisting of" shall mean that the devices, systems, and methods include the recited elements and exclude anything more than a trivial or inconsequential element or step. Embodiments defined by each of these transitional terms are within the scope of this disclosure.

The systems and methods of the embodiments described herein and variations thereof can be embodied and/or implemented at least in part as a machine for receiving a computer-readable medium storing computer-readable instructions. The instructions may be executed by computer-executable components integrated with the system and one or more portions of the processor on the wearable device and/or computing device. In some embodiments, the instructions may be executed by computer-executable components that are in communication with the wearable device. The computer-readable medium can be stored on any suitable computer-readable media such as RAMs, ROMs, flash memory, EEPROMs, optical devices (e.g., an image or DVD), hard drives, floppy drives, or any suitable device. The computer-executable component may be a general or application-specific processor, but any suitable dedicated hardware or hardware/firmware combination can alternatively or additionally execute the instructions.

As used in the description and claims, the singular form "a", "an" and "the" include both singular and plural references unless the context clearly dictates otherwise. For example, the term "sensor" may include, and is contemplated to include, a plurality of sensors. At times, the claims and disclosure may include terms such as "a plurality," "one or more," or "at least one;" however, the absence of such terms is not intended to mean, and should not be interpreted to mean, that a plurality is not conceived.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A computer-implemented method for performing non-invasive blood glucose monitoring of a subject, the method comprising:

providing a noninvasive wearable device positioned substantially adjacent to a body site of the subject and comprising a near infrared light source;

causing the light source to illuminate the body site of the subject;

receiving at least one digital image representing reflected light from the body site, the at least one digital image being captured by an optical sensor of the wearable device;

programmatically analyzing the at least one digital image using at least one processor to assess blood glucose for the subject, the analyzing comprising:

determining a visual appearance of at least one venous blood vessel in the at least one digital image, by one or more machine learning models comprising a deep learning network trained to learn representations of venous blood vessel features from clinical data comprising digital images of venous blood vessels of a plurality of subjects and metabolic measurements obtained from metabolic panel testing of blood samples drawn from the plurality of subjects, the metabolic measurements comprising glucose measurements and one or more of sodium, potassium, bicarbonate, and blood urea nitrogen measurements, the determining comprising:

detecting, in the at least one digital image, changes in a size or volume of the at least one venous blood vessel;

detecting, in the at least one digital image, changes in a darkness or intensity of pixels representing the at least one venous blood vessel based on infrared light interactions between the optical sensor and the body site;

detecting, in the at least one digital image, features of the at least one venous blood vessel, the features comprising edges, sizes, shapes, and color contrast of the at least one venous blood vessel; and classifying the detected changes in size or volume and the detected changes in darkness or intensity of pixels associated with the detected features into a blood glucose estimate range;

generating an indication based on the blood glucose estimate range, wherein the indication comprises personalized actionable instructions for the subject based on the blood glucose estimate range, the personalized actionable instructions comprising feedback on how one or more of diet, exercise, sleep, stress, and medications affect blood glucose of the subject to enable the subject to adjust lifestyle choices.

2. The computer-implemented method of claim 1, wherein the blood glucose estimate range is expressed as one of: a range of values, a category in a plurality of categories, or a measurement estimated to be accurate within a predefined margin of error.

3. The computer-implemented method of claim 1, wherein the light source is a near infrared light source having wavelengths ranging from about 700 nm to about 1200 nm.

4. The computer-implemented method of claim 1, wherein the indication representing the blood glucose estimate range comprises application data configured to present a blood glucose estimate to the subject in one or more of: an email, a display screen, a text message, an audio entry, and a visual indicator within a computing device associated with the subject or a care provider of the subject.

5. The computer-implemented method of claim 1, further comprising:

monitoring, the subject over time, the monitoring including:

causing the light source to illuminate the body site according to a predefined schedule;

receiving additional digital images of the body site during the monitoring; and programmatically analyzing the additional digital images to determine a plurality of blood glucose estimates for the subject; and generating a visual mapping depicting the blood glucose estimate range and the plurality of additional blood glucose estimates in a time-based graph.

6. The computer-implemented method of claim 1, further comprising:

monitoring the subject over time;

receiving additional digital images of the body site during the monitoring;

generating a first set of measurements associated with the detected features in the at least one digital image corresponding to a first point in time;

generating a second set of measurements for at least one image of the additional digital images corresponding to the body site, the second set of measurements corresponding to portions of the at least one venous blood vessel at a second point in time; and comparing the first set of measurements to the second set of measurements to determine an updated glucose measurement for the subject.

7. The computer-implemented method of claim 1, wherein the body site is a volar wrist of the subject and wherein the at least one digital image is captured by the optical sensor installed on the wearable device configured to be positioned on or adjacent to the volar wrist of the subject.

8. The computer-implemented method of claim 1, wherein:

the body site is a dextral volar wrist of the subject and the light source and the sensor are positioned on a sinistral dorsal wrist and facing away from the sinistral dorsal wrist; and the at least one digital image is of at least a portion of the dextral volar wrist that is captured in response to detecting that the dextral volar wrist is within a predefined range from the light source.

9. The computer-implemented method of claim 1, further comprising:

obtaining a plurality of digital images of the body site captured over time;

programmatically analyzing the at least one digital image against the obtained plurality of digital images of the body site captured over time to ascertain changes in blood glucose levels of the subject in response to an event occurring during the time, wherein the event is one or more of: a meal, a fast, a physical stressor, an emotional stressor, a sleep event, a time of day, and a change in estrogen.

10. The computer-implemented method of claim 1, wherein the changes in the size or volume are based on a determined concentration of osmotic solutes in blood serum or blood plasma, the osmotic solutes including sodium ion, chloride, bicarbonate, glucose, and urea.

11. The computer-implemented method of claim 1, wherein determining the visual appearance comprises detecting changes in an appearance of the at least one venous blood vessel and changes in a light absorption property of water and glucose associated with the at least one venous blood vessel.

12. The computer-implemented method of claim 1, wherein generating the indication further comprises:

setting targets for the subject to achieve specific glycemic control, and providing, for presentation in a display of the wearable device, graphical content marking hypoglycemic and hyperglycemic boundaries.

13. The computer-implemented method of claim 1, wherein:

the wearable device is worn on a first wrist of the subject;

the light source is positioned on a surface of the wearable device facing away from the first wrist;

the body site is a second wrist of the subject opposite the first wrist;

the method further comprises detecting that the second wrist is within a predefined range from the light source and the at least one digital image is captured in response to detecting that the second wrist is within the predefined range.

14. The computer-implemented method of claim 1, further comprising:

continuously monitoring the subject over a predetermined time period by:

repeatedly causing the light source to illuminate the body site at regular intervals, capturing a time-series of digital images at the regular intervals, for each digital image in the time-series, detecting physical changes in the at least one venous blood vessel comprising changes in a size or volume of the at least one venous blood vessel and changes in darkness or intensity of pixels representing the at least one venous blood vessel, determining, from the detected physical changes, a temporal pattern of blood glucose fluctuations, and generating a time-based graphical visualization depicting the temporal pattern with marked hypoglycemic and hyperglycemic boundaries.

15. The computer-implemented method of claim 1, wherein determining the visual appearance further comprises:

applying, by the at least one processor, an edge detection algorithm to detect edges of the at least one venous blood vessel in the at least one digital image;

extracting, based on the detected edges, image portions representing the at least one venous blood vessel;

aligning the extracted image portions from digital images captured at different times to track the at least one venous blood vessel over time;

measuring changes in the size or volume of the at least one venous blood vessel between a first image at a first time and a second image at a second time; and mapping the measured changes in the size or volume to corresponding changes in glucose levels using stored mapping logic.

16. The computer-implemented method of claim 1, further comprising: segmenting, by a second machine learning model, the at least one digital image into a plurality of regions to detect the at least one venous blood vessel and identifying and labeling pixels in the at least one digital image corresponding to the at least one venous blood vessel and to distinguish the at least one venous blood vessel from surrounding tissue.

17. The computer-implemented method of claim 1, wherein the changes in the darkness or intensity of pixels representing the at least one venous blood vessel are based on a reduced scattering coefficient of near infrared light in a presence of glucose molecules in the at least one venous blood vessel.

18. The computer-implemented method of claim 1, wherein the programmatically analyzing further comprises determining, by the one or more machine learning models, that physiological changes in glucose detected in the at least one digital image are based on venous blood at the body site, wherein the blood glucose estimate range is generated based on the physiological changes in glucose attributable to the venous blood.

19. The computer-implemented method of claim 1, wherein generating the indication further comprises predicting, based on a temporal pattern of blood glucose estimate ranges determined from a plurality of digital images captured over time, a likelihood of a blood glucose event comprising one or more of a hypoglycemic event, a hyperglycemic event, or a prediabetes or diabetes onset, and generating the personalized actionable instructions before the predicted blood glucose event occurs.

20. The computer-implemented method of claim 1, further comprising: analyzing physical changes in the detected features in the at least one venous blood vessel as reflected in pixels representing the at least one venous blood vessel across images captured at different times.

21. The computer-implemented method of claim 1, wherein the changes in the size or the volume of the at least one venous blood vessel represent osmolality changes in which fluid moves between plasma and intracellular compartments, wherein osmolality depends on a concentration of osmotic solutes in blood serum or blood plasma comprising sodium, glucose, and urea.

22. A noninvasive blood glucose monitoring system comprising:

a wearable device configured to be removably coupled to a body site of a subject, the wearable device comprising:

at least one optical sensor communicatively coupled to at least one near infrared light source, the at least one optical sensor configured to sense reflected light from the body site resulting in capturing an image; and at least one processor communicatively coupled to the wearable device and configured to programmatically analyze the image to determine a blood glucose estimate for the subject, wherein the analyzing comprises:

determining, by one or more machine learning models comprising a deep learning network trained to learn representations of venous blood vessel features from clinical data comprising digital images of venous blood vessels of a plurality of subjects and metabolic measurements obtained from metabolic panel testing of blood samples drawn from the plurality of subjects, the metabolic measurements comprising glucose measurements and one or more of sodium, potassium, bicarbonate, and blood urea nitrogen measurements, the determining comprising:

detecting, in the image, changes in a size or volume of the at least one venous blood vessel;

detecting, in the image, changes in a darkness or intensity of pixels representing the at least one venous blood vessel based on infrared light interactions between the optical sensor and the body site;

detecting, in the image, features of the at least one venous blood vessel, the features comprising edges, sizes, shapes, and color contrast of the at least one venous blood vessel; and classifying the detected changes in size or volume and the detected changes in darkness or intensity of pixels associated with the detected features into a blood glucose estimate range;

generating an indication based on the blood glucose estimate range, wherein the indication comprises personalized actionable instructions for the subject, the personalized actionable instructions comprising feedback on how one or more of diet, exercise, sleep, stress, and medications affect blood glucose of the subject to enable the subject to adjust lifestyle choices to achieve specific glycemic control.

23. The noninvasive blood glucose monitoring system of claim 22, wherein the body site is an upper extremity of the subject, and the wearable device is configured to be positioned on or adjacent to the upper extremity.

24. The noninvasive blood glucose monitoring system of claim 22, wherein the analyzing further comprises:

monitoring the subject over time to capture additional images;

programmatically analyzing the additional images to determine a plurality of additional blood glucose estimates for the subject; and generating a visual mapping depicting the blood glucose estimate range and the plurality of additional blood glucose estimates in a time-based graph;

providing, for presentation in a display of the wearable device or a display of a computing device, the time-based graph.

25. The noninvasive blood glucose monitoring system of claim 22, wherein the analyzing further comprises:

monitoring the subject over time;

receiving additional images of the body site during the monitoring;

generating a first set of measurements associated with the detected features in the image corresponding to a first point in time;

generating a second set of measurements for at least one image of the additional images corresponding to the body, the second set of measurements corresponding to portions of the body site at a second point in time; and comparing the first set of measurements to the second set of measurements to determine an updated glucose measurement for the subject.

26. The noninvasive blood glucose monitoring system of claim 22, wherein:

the at least one processor is further configured to continuously monitor the subject over a predetermined time period by:

repeatedly causing the at least one near infrared light source to illuminate the body site at regular intervals, capturing a time-series of images at the regular intervals via the optical sensor, for each image in the time-series, detecting physical changes in the at least one venous blood vessel comprising changes in a size or volume of the at least one venous blood vessel and changes in darkness or intensity of pixels representing the at least one venous blood vessel, determining, from the detected physical changes, a temporal pattern of blood glucose fluctuations; and a display associated with the wearable device or another computing device is further configured to present a time-based graphical visualization depicting the temporal pattern with marked hypoglycemic and hyperglycemic boundaries.

27. The noninvasive blood glucose monitoring system of claim 22, wherein:

the wearable device is configured to be worn on a first wrist of the subject;

the optical sensor and the at least one near infrared light source are positioned on a surface of the wearable device facing away from the first wrist;

the at least one processor is configured to:

detect when a second wrist of the subject opposite the first wrist is within a predefined range from the optical sensor, in response to detecting that the second wrist is within the predefined range, automatically cause the at least one near infrared light source to illuminate the second wrist and cause the optical sensor to capture the image of the second wrist, and determine the blood glucose estimate range from the image of the second wrist.

28. A method for performing noninvasive blood glucose monitoring of a subject, the method comprising:

causing an infrared light source to illuminate a body site of the subject;

receiving at least one digital image representing reflected light from the body site, the at least one digital image being captured by an optical sensor provided substantially adjacent to the body site;

programmatically analyzing, by a processor, the at least one digital image to assess blood glucose for the subject, wherein the processor executes one or more machine learning models comprising a deep learning network comprising a plurality of layers and trained to learn representations of venous blood vessel features from clinical data comprising digital images of venous blood vessels of a plurality of subjects and corresponding metabolic measurements obtained from metabolic panel testing of blood samples drawn from the plurality of subjects, the analyzing comprising:

receiving an analysis output comprising one or more identified venous blood vessel portions in the at least one digital image, and a visual appearance assessment of the one or more identified venous blood vessel portions, the visual appearance assessment comprising:

detecting, in the at least one digital image, changes in a size or volume of the one or more identified venous blood vessel;

detecting, in the at least one digital image, changes in a darkness or intensity of pixels representing the one or more identified venous blood vessel based on reflected light from the infrared light causing interactions between the optical sensor and the body site;

detecting, in the at least one digital image, features of the one or more identified venous blood vessel, the features comprising edges, sizes, shapes, and color contrast of the one or more identified venous blood vessel; and classifying the detected changes in size or volume and the detected changes in darkness or intensity of pixels associated with the detected features into a blood glucose estimate range; and generating an indication representing the blood glucose estimate range, wherein the indication comprises personalized actionable instructions for the subject based on the blood glucose estimate range, the personalized actionable instructions comprising feedback on how one or more of diet, exercise, sleep, stress, and medications affect blood glucose of the subject to enable the subject to adjust lifestyle choices, wherein the metabolic measurements comprise glucose measurements and one or more of sodium, potassium, bicarbonate, and blood urea nitrogen measurements.

29. The method of claim 28, further comprising monitoring, the subject over time, to capture a plurality of additional images;

programmatically analyzing the additional images to determine a plurality of additional blood glucose estimates for the subject; and generating a visual mapping depicting the blood glucose estimate range and the plurality of additional blood glucose estimates in a time-based graph.

* * * * *